(12) United States Patent
Ataman-Onal et al.

(10) Patent No.: US 9,433,674 B2
(45) Date of Patent: Sep. 6, 2016

(54) COMPOSITION COMPRISING A COLLOIDAL SYNTHETIC BIORESORBABLE VECTOR AND A VIRAL VECTOR

(71) Applicant: CENTRE NATIONAL DE LA RECHERCHE SCIENTIFIQUE, Paris (FR)

(72) Inventors: Yasemin Ataman-Onal, Lyons (FR); Thierry Delair, Echalas (FR); Bernard Verrier, Mornant (FR)

(73) Assignee: CENTRE NATIONALE DE RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/620,920

(22) Filed: Feb. 12, 2015

(65) Prior Publication Data
US 2015/0150967 A1    Jun. 4, 2015

Related U.S. Application Data

(62) Division of application No. 12/084,970, filed as application No. PCT/FR2006/051039 on Oct. 17, 2006, now abandoned.

(30) Foreign Application Priority Data

Nov. 14, 2005  (FR) ..................... 05 53445

(51) Int. Cl.
| | | |
|---|---|---|
| *A61K 35/00* | (2006.01) | |
| *C12N 15/63* | (2006.01) | |
| *A61K 39/39* | (2006.01) | |
| *A61K 39/21* | (2006.01) | |
| *A61K 47/48* | (2006.01) | |
| *A61K 39/12* | (2006.01) | |
| *A61K 39/235* | (2006.01) | |
| *A61K 39/285* | (2006.01) | |
| *C12N 7/00* | (2006.01) | |
| *A61K 39/00* | (2006.01) | |
| *A61K 47/34* | (2006.01) | |

(52) U.S. Cl.
CPC ........... *A61K 39/39* (2013.01); *A61K 39/0011* (2013.01); *A61K 39/12* (2013.01); *A61K 39/21* (2013.01); *A61K 39/235* (2013.01); *A61K 39/285* (2013.01); *A61K 47/482* (2013.01); *A61K 47/48792* (2013.01); *A61K 47/48853* (2013.01); *A61K 47/48876* (2013.01); *C12N 7/00* (2013.01); *A61K 39/00* (2013.01); *A61K 47/34* (2013.01); *A61K 2039/523* (2013.01); *A61K 2039/5254* (2013.01); *A61K 2039/5256* (2013.01); *A61K 2039/53* (2013.01); *A61K 2039/54* (2013.01); *A61K 2039/543* (2013.01); *A61K 2039/545* (2013.01); *A61K 2039/55505* (2013.01); *A61K 2039/55511* (2013.01); *A61K 2039/55555* (2013.01); *A61K 2039/55583* (2013.01); *A61K 2039/57* (2013.01); *A61K 2039/575* (2013.01); *A61K 2039/6087* (2013.01); *A61K 2039/6093* (2013.01); *C12N 2710/10041* (2013.01); *C12N 2710/10071* (2013.01); *C12N 2710/10343* (2013.01); *C12N 2710/24141* (2013.01); *C12N 2710/24143* (2013.01); *C12N 2710/24171* (2013.01); *C12N 2740/16034* (2013.01); *C12N 2740/16071* (2013.01); *C12N 2740/16234* (2013.01)

(58) Field of Classification Search
None
See application file for complete search history.

(56) References Cited

U.S. PATENT DOCUMENTS

| | | | |
|---|---|---|---|
| 6,013,638 A | 1/2000 | Crystal et al. | |
| 6,099,831 A | 8/2000 | Perricaudet et al. | |
| 6,824,793 B1 * | 11/2004 | O'Hagan et al. ............. | 424/491 |
| 2007/0059681 A1 | 3/2007 | Ataman-Onal et al. | |

FOREIGN PATENT DOCUMENTS

| | | |
|---|---|---|
| WO | 98/56919 A2 | 12/1998 |
| WO | 99/30733 A1 | 6/1999 |
| WO | 02/26209 A2 | 4/2002 |
| WO | 2005/027871 A2 | 3/2005 |

OTHER PUBLICATIONS

Ramsburg et al., "Highly Effective Control of an AIDS Virus Challenge in Macaques by Using Vesicular Stomatitis Virus and Modified Vaccinia Virus Ankara Vaccine Vectors in a Single-Boost Protocol," Journal of Virology, vol. 78, No. 8, pp. 3930-3940, Apr. 2004.

Hanke et al., "Effective Induction of Simian Immunodeficiency Virus-Specific Cytotoxic T Lymphocytes in Macaques by Using a Multiepitope Gene and DNA Prime-Modified Vaccinia Virus Ankara Boost Vaccination Regimen," Journal of Virology, vol. 73, No. 9, pp. 7524-7532, Sep. 1999.

(Continued)

*Primary Examiner* — Celine Qian
(74) *Attorney, Agent, or Firm* — Oliff PLC

(57) ABSTRACT

A method of vaccination against a viral, bacterial or non-infectious disease includes administering an effective dose of a prime vaccine and then an effective dose of a boost vaccine. Each one of the prime vaccine and the boost vaccine includes an active principle. The prime vaccine includes, as the active principle, a colloidal synthetic bioresorbable vector that includes at least one protein substance. The boost vaccine includes, as the active principle, a viral vector that includes at least one nucleotide sequence which codes for a protein substance corresponding to the at least one protein substance of the synthetic vector.

18 Claims, 10 Drawing Sheets

(56) References Cited

OTHER PUBLICATIONS

Nikou et al., "A HER-2/neu Peptide Admixed with PLA Microspheres Induces a Th 1-biased Immune Response in Mice," Biochimica et Biophysica Acta, vol. 1725, pp. 182-189, 2005.

Flynn et al., "Immunization with HIV Gag Targeted to Dendritic Cells Followed by Recombinant New York Vaccinia Virus Induces Robust T-Cell Immunity in Nonhuman Primates," PNAS, vol. 108, No. 17, pp. 7131-7136, Apr. 26, 2011.

Hutchings et al., "Novel Protein and Poxvirus-Based Vaccine Combinations for Simultaneous Induction of Humoral and Cell-Mediated Immunity," The Journal of Immunology, vol. 175, pp. 599-606, 2005.

Chong et al., "Enhancement of T Helper Type 1 Immune Responses Against Hepatitis B Virus Core Antigen by PLGA Nanoparticle Vaccine Delivery," Journal of Controlled Release, vol. 102, pp. 85-99, 2005.

Shahin et al., "Heterologous Prime-Boost Immunisation Regimens Against Infectious Diseases," Human Protection and Performance Division, DSTO Defence Science and Technology Organization, DSTO-GD-0474, pp. 1-32, Aug. 2006.

Jiang et al., "Biodegradable Poly(lactic-co-glycolic acid) Microparticles for Injectable Delivery of Vaccine Antigens," Advanced Drug Delivery Reviews, vol. 57, pp. 391-410, 2005.

Dunachie et al., "A Clinical Trial of Prime-Boost Immunisation with the Candidate Malaria Vaccines RTS,S/AS02A and MVA-CS," Vaccine, vol. 24, pp. 2850-2859, 2006.

Tritel et al., "Prime-Boost Vaccination with HIV-1 Gag Protein and Cytosine Phosphate Guanosine Oligodeoxynucleotide, Followed by Adenovirus, Induces Sustained and Robust Humoral and Cellular Immune Responses," The Journal of Immunology, vol. 171, pp. 2538-2547, 2003.

Dunachie et al., "Prime-Boost Strategies for Malaria Vaccine Development," The Journal of Experimental Biology, vol. 206, pp. 2771-3779, 2003.

McShane et al., "Prime-Boost Immunisation Strategies for Tuberculosis," Microbes and Infection, vol. 7, pp. 962-967, 2005.

Woodland, "Jump-Starting the Immune System: Prime-Boosting Comes of Age," Review, Trends in Immunology, vol. 25, No. 2, pp. 98-104, Feb. 2004.

Schagen et al., "Immune responses against adenoviral vectors and their transgene products: a review of strategies for evasion," Critical Reviews in Oncology/Hematology, 2004, vol. 50, pp. 51-70.

Negri et al., "Protective efficacy of a multicomponent vector vaccine in cynomolgus monkeys after intrarectal simian immunodeficiency virus challenge," Journal of General Virology, 2004, vol. 85, pp. 1191-1201.

Otten et al., "Induction of Broad and Potent Anti-Human Immunodeficiency Virus Immune Responses in Rhesus Macaques by Priming with a DNA Vaccine and Boosting with Protein-Adsorbed Polylactide Coglycolide Microparticles," Journal of Virology, 2003, vol. 77, No. 10, pp. 6087-6092.

O'Hagan et al., "Induction of Potent Immune Responses by Cationic Microparticles with Adsorbed Human Immunodeficiency Virus DNA Vaccines," Journal of Virology, 2001, vol. 75, No. 19, pp. 9037-9043.

Benita et al., "Submicron Emulsions as Colloidal Drug Carriers for Intravenous Administration: Comprehensive Physicochemical Characterization," Journal of Pharmaceutical Sciences, 1993, vol. 82, No. 11, pp. 1069-1079.

Trotta et al., "Preparation of solid lipid nanoparticles by a solvent emulsification-diffusion technique," International Journal of Pharmaceutics, 2003, vol. 257, pp. 153-160.

Jiang et al., "Biodegradable poly(lactic-co-glycolic acid) microparticles for injectable delivery of vaccine antigens," Advanced Drug Delivery Reviews, 2005, vol. 57, pp. 391-410.

Wang et al., "Active Immunotherapy of Cancer with a Nonreplicating Recombinant Fowlpox Virus Encoding a Model Tumor-Associated Antigen," The Journal of Immunology, 1995, vol. 154, pp. 4685-4692.

"Recombinant Dna Technology I," Annals of the New York Academy of Sciences, 1991, vol. 646.

Tamber et al., "Formulation aspects of biodegradable polymeric microspheres for antigen delivery," Advanced Drug Delivery Review, 2005, vol. 57, pp. 357-376.

"Protein immobilization Fundamentals and Applications," 1991, pp. iii-ix.

Adra et al., "Cloning and expression of the mouse pgk-1 gene and the nucleotide sequence of its promoter," Gene, 1987, vol. 60, pp. 65-74.

Moessler et al., "The SM 22 promoter directs tissue-specific expression in arterial but not in venous or visceral smooth muscle cells in transgenic mice," Development, 1996, vol. 122, pp. 2415-2425.

Reddy et al., "Nucleotide Sequence, Genome Organization, and Transcription Map of Bovine Adenovirus Type 3," Journal of Virology, 1998, vol. 72, No. 2, pp. 1394-1402.

Kelly et al., "Use of Nondefective Adenovirus-Simian Virus 40 Hybrids for Mapping the Simian Virus 40 Genome," Journal of Virology, 1973, vol. 12, No. 3, pp. 643-652.

Yei et al., "In Vivo Evaluation of the Safety of Adenovirus-Mediated Transfer of the Human Cystic Fibrosis Transmembrane Conductance Regulator cDNA to the Lung," Human Gene Therapy, 1994, vol. 5, pp. 731-744.

Dai et al., "Cellular and humoral immune responses to adenoviral vectors containing factor IX gene: Tolerization of factor IX and vector antigens allows for long-term expression," Proc. Natl. Acad. Sci. USA, 1995, vol. 92, pp. 1401-1405.

Goebel et al., "The Complete DNA Sequence of Vaccinia Virus," Virology, 1990, vol. 179, pp. 247-266 and 517-563.

Antoine et al., "The Complete Genomic Sequence of the Modified Vaccinia Ankara Strain: Comparison with Other Orthopoxviruses," Virology, 1998, vol. 244, pp. 365-396.

Mayr et al., "Abstammung, Eigenschaften and Verwendung des attenuierten Vaccinia-Stammes MVA," Infection, 1975, vol. 3, pp. 6-14.

Yee et al., "A general method for generation of high-titer, pantropic retroviral vectors: Highly efficient infection of primary hepatocytes," Proc. Natl. Acad. Sci. USA, 1994, vol. 91, No. 20, pp. 9564-9568.

Cheynet et al., "Overexpression of HIV-1 Proteins in *Escherichia coli* by a Modified Expression Vector and Their One-Step Purification," Protein Expression and Purification, 1993, vol. 4, No. 5, pp. 367-372.

Sharpe et al., "Muscosal immunization with PLGA-microencapsulated DNA primes a SIV-specific CTL response revealed by boosting with cognate recombinant modified vaccinia virus Ankara", Virology, 2003, vol. 313, No. 1, pp. 13-21.

Gander, "Trends in particulate antigen and DNA delivery systems for vaccines", Advanced Drug Delivery Reviews, 2005, vol. 57, No. 3, pp. 321-323.

"Biodegradable microspheres prolong antigen presentation by macrophages", Vaccine Weekly, 2006.

Major et al., "The Molecular Virology of Hepatitis C," Hepatology, 1997, vol. 25, No. 6, pp. 1527-1538.

Houghton, "Cancer Antigens: Immune Recognition of Self and Altered Self," Journal of Exp. Med., 1994, vol. 180, pp. 1-4.

Biomaterial, vol. 22, pp. 394-399, 2004.

Hu et al., "Protection of Macaques Against SIV Infection by Subunit Vaccines of SIV Envelope Glycoprotein gp160," Science, Aug. 28, 1991, vol. 255, pp. 456-459.

Israel et al., "Combined Systemic and Mucosal Immunization with Microsphere-Encapsulated Inactivated Simian Immunodeficiency Virus Elicits Serum, Vaginal, and Tracheal Antibody Responses in Female Rhesus Macaques," AIDS Research and Human Retroviruses, 1991, vol. 15, No. 12, pp. 1121-1136, Mary Ann Liebert, Inc.

Otten et al., "Enhanced Potency of Plasmid DNA Microparticle Human Immunodeficiency Virus in Rhesus Macaques by Using a Priming-Boosting Regimen with Recombinant Proteins," Journal of Virology, Jul. 2005, vol. 79, No. 13, pp. 8189-8200, American Society for Microbiology.

Moldoveanu et al., "Oral Immunization with Influenza Virus in Biodegradable Microspheres," The Journal of Infectious Diseases, 1993, vol. 167, pp. 84-90, The University of Chicago.

Mar. 9, 2007 International Search Report issued in International Application No. PCT/FR2006/051039.

\* cited by examiner

COMPOSITION COMPRISING A COLLOIDAL SYNTHETIC BIORESORBABLE VECTOR AND A VIRAL VECTOR

This is a divisional of application Ser. No. 12/084,970 filed May 14, 2008, which is a National Stage Application of PCT/FR2006/051039 filed Oct. 17, 2006, and claims the benefit of French Application No. 0553445 filed Nov. 14, 2005. The entire disclosures of the prior applications are hereby incorporated by reference in their entirety.

The present invention relates to the field of prophylactic and therapeutic vaccination. In particular, the present invention relates to a vaccine composition comprising a viral vector enabling expression of protein substances and a synthetic vector having protein substances.

Historically, the antigens used in the vaccines are either living microorganisms, the pathogenic power of which has been attenuated, or killed microorganisms. However, these vaccines often cause undesirable secondary effects during administration and in rare cases they cause very serious complications. Thus for a number of years in order to ensure vaccine safety priority is given to the use of purified fractions of microorganisms in vaccines. Such an immunogen, administered alone, can sometimes not induce a sufficient immune response. According to the prior art numerous vaccine strategies have been developed in order to increase or orient the immune response induced by the purified immunogens present in a vaccine.

The most direct strategy is to combine the relevant protein substance (immunogen) with an adjuvant. Although numerous types of adjuvants are being developed, until recently aluminium hydroxides (alum) were the only adjuvant allowed for administration to humans. However, alum is a weak adjuvant for inducing humoral responses, it is not appropriate for all antigens and does not enable cell responses to be obtained. Amongst the adjuvant currently being developed, the most effective systems for inducing strong immunity are synthetic vectors based on microparticles and in particular microparticles of polylactic-co-glycolic acid (PLGA) and polylactic acid (PLA). Due to their size these particles make it possible to target antigen presenting cells such as macrophages or dendritic cells and improve the take-up of the immunogen by the immune system. The protein substance can be either encapsulated in the microparticles or adsorbed on the surface. The two approaches make it possible to induce both cellular and humoral immune responses, even if they were originally used above all in order to obtain an antibody response. However, encapsulation has two major drawbacks. The first is that a partial or total degradation of the microparticles is required for the protein substance to become available to the immune system, also the establishment of immunity is delayed. The second drawback is that the protein substance can be denatured or degraded during encapsulation and thus can lose its immunogenic properties. For these reasons this process cannot be used with every type of protein substance, whilst the process by adsorption does not have these drawbacks. In the two cases, the major obstacle to their use is their lack of effectiveness for generating specific cell responses. If by comparison with alum the cell responses induced are even better, they are well below what can be obtained with a viral vector.

Recombinant viral vectors enable expression in vivo (in animals or in humans) of the relevant protein substance. This is an effective strategy which enables good mobilisation of the immune system. However, the induction of a lasting immune response necessitates the use of attenuated living vectors which can replicate in the vaccinated organism. For statutory reasons associated with the safe use of vaccines, new generations of vaccines use viral vectors which are non-replicative in humans, resulting in a diminution of the specific immune responses in time. Thus in the case of prophylactic vaccines it is still sometimes necessary to restimulate the specific immunity in order to maintain an effective memory response. In the field of immunotherapy, restimulation of the specific immunity remains useful for maintaining the intensity of the immune responses which enable control of the pathogenic organism. Thus the repeated administration of viral vectors appears necessary but is accompanied by a major problem which is the problem of anti-vector immunity. For the viral vector is itself an immunogen and as it is administered several times the specific immunity of the vector appears and then increases. This immune response is intended to eliminate the viral vector and also prevents the expression of the gene which it carries, thus resulting in a decrease in the effectiveness of the immune responses against the relevant protein substance. Moreover, the anti-vector immunity prevents the use of the vector in question for vaccination against another disease. Schagen et al describe certain approaches which make it possible to alleviate this anti-vector immunity, such as modifications at the level of the vector or even adaptations at the level of the vaccinated patients (2004, Critical Reviews in Oncology/Hematology 50:51-70). However, the implementation of these approaches is difficult and cannot be achieved for all diseases or all patients. Therefore the strategy which uses viral vectors is not optimised.

Another way of improving the immune response induced by vaccination is the prime-boost strategy. It consists of increasing the specific immune responses by administering sequentially two different vaccines which carry one and the same protein substance instead of administering the same vaccine several times. For example, it is possible to use a different viral vector at each injection (Negri D R, et al, 2004, Journal of General Virology, 85: 1191-1201). However, this strategy only has a few chances of success because the number of viral vectors which are authorised for use in humans is very restricted. Moreover, the repeated administration of these viral vectors again encounters the problem of anti-vector immunity. In order to circumvent this problem, Otten et al describe the use of a DNA prime followed by a boost of PLGA microparticles with protein antigens adsorbed on the surface thereof (2003, Journal of Virology, 77: 6087-6092). Sharpe et al proposed a DNA prime encapsulating DNA in PLGA-based microparticles and a boost by a viral vector MVA (2003, Virology, 313: 13-21). O'Hagan et al describe the use of a prime by the DNA adsorbed on PLGA microparticles, followed by a boost by a vaccine vector (2001, Journal of Virology, 75: 9037-9043). Patent Application WO98/56919A describes a DNA prime followed by a boost by a poxvirus. The drawback of the use of a DNA prime is its low effectiveness particularly in primates and also when the gene is not very immunogenic such as for example the HIV-1 Tat gene. Patent Application WO98/56919A also describes the use of a prime by VLPs (virus-like particles), followed by a boost by a poxvirus. The VLPs are defective viral particles which do not incorporate the viral genome and which cannot reproduce. They are often formed by self-assembly of the structural proteins of a virus or of a retrotransposon (endogenous element similar to a retrovirus) such as the precursor Pr55 Gag of HIV-1 or the proteins L1 and L2 of HPV-16 (human papilloma virus). As a function of the viral proteins expressed the structure of the VLP may be close to or less than that of the native virion, such that the VPLs are comparable to a virus. The drawback of these VLPs is that that they are the result of biotechnology and that their manufacture according to the statutory standards is very difficult.

The Applicants have now demonstrated, against all expectations, that the particular association of a colloidal synthetic bioresorbable vector comprising protein substances, and a viral vector comprising the nucleotide sequences which code for the corresponding protein substances, makes it possible to increase the effectiveness of the vaccination associated with the use of a protein substance, whilst decreasing the anti-vector immunity.

Thus a first object of the invention consists of a pharmaceutical composition comprising or consisting of:

a colloidal synthetic bioresorbable vector comprising at least one protein substance, a viral vector comprising at least one nucleotide sequence which codes for a protein substance corresponding to at least one protein substance of the synthetic vector, optionally in association with a pharmaceutically acceptable excipient.

Another object of the invention consists of the use of the said composition for the preparation of a medicament, preferably a vaccine. It can also be used for the in vitro diagnosis of pathological states relating to the protein substances of the composition according to the invention.

The present invention therefore proposes a novel composition comprising a colloidal synthetic bioresorbable vector having at least one protein substance.

A bioresorbable compound is understood to be a compound which is not toxic, that is to say a compound of which the administration in the organism does not cause a lethal, disabling or inconvenient physiological or metabolic modification in day-to-day living, and which can be eliminated by natural means from the organism after administration.

The terms colloid and colloidal define any dispersion of a substance (dispersed phase) within an aqueous continuous phase of which at least one of the three dimensions is less than or equal to 10 μm and preferably less than or equal to 1 μm.

An aqueous continuous phase is a phase of which the composition is principally water, such as for example a buffer or a water-miscible water/organic solvent mixture. Of course, an aqueous continuous phase appropriate to the purposes of the invention is a non-toxic phase.

The disperse phase can be a liquid which is insoluble in the continuous phase such as for example an oil or a mixture of oils, or organic fatty materials, or it can even be a polymeric or mineral solid. The disperse phase is always bioresorbable.

Examples of the disperse phase include olive oil, sunflower oil, groundnut oil, rapeseed oil, or mixtures thereof; triglycerides; synthetic polymers such as polymers of hydroxyacid such as for example lactic acid, glycolic acid, hydroxybutyric acid, or compounds resulting from caprolactone; polypeptides such as the compounds resulting from caprolactone polymerisation; natural polymers such as for example polysaccharides such as hyaluronic acid, chitosan, or dextran.

Examples of such bioresorbable colloids are given in Benita A. and Levy M. Y., 1993, Journal of Pharmaceutical Sciences, 82(11): 1069-1079 (liquid/liquid emulsions), Trona M., et al, 2003, International Journal of Pharmaceutics, 257: 152-160 (lipid solid/liquid emulsions), and Jiang W., et al, 2005, Biodegradable poly(lactic-co-glycolic) acid microparticles for injectable delivery of vaccine antigens Advanced Drug Delivery Reviews, 57: 391, 410.

The form of the colloidal synthetic vector is given by the disperse phase which may or may not be spherical, which may be homogeneous or may be constituted by a stack of laminas.

The synthetic vector according to the invention is preferably of spherical nature. Even more preferably the vector is composed of microspheres. The terms microsphere and microparticle are used indiscriminately in the following description. A microparticle or microsphere is understood to mean a particle of a size at most in the micron range to enable them to enter the antigen presenting cells. A size at most in the micron range is understood to be a dimension smaller than or equal to 999 μm. Microparticics preferably have a particle diameter smaller than or equal to 3 μm. Even more preferably the particles according to the invention have a submicron size, preferably with a diameter between 150 and 900 nm, more preferably between 250 and 700 nm. The size of the particles is easily determined by techniques known to the person skilled in the art such as, for example, by using scanning electron microscopy, quasi-elastic scattering of light or transmission electron microscopy.

According to one embodiment of the invention the colloidal synthetic vectors are polymer-based vectors.

By way of example of polymer-based synthetic vectors, mention may be made of vectors comprising microparticles based on polymers such as poly(α-hydroxy acids), polyhydroxybutyric acids, polycaprolactones, polyorthoesters and polyanhydrides. The synthetic vector preferably comprises at least one bioresorbable polymer chosen from amongst a poly(α-hydroxy acid) such as poly(D-lactic acid), poly(L-lactic acid) (both known as PLA), polyglycolic acid (known as PLG), or a mixture of poly(α-hydroxy acids) such as a mixture of poly(D- and L-lactic acids), a mixture of poly (L-lactic acid) and polyglycolic acid, a mixture of poly(D-lactic acid) and polyglycolic acid, or a mixture of poly(D- and L-lactic acids) and polyglycolic acid. When the polymer is a mixture of poly(α-hydroxy acids) the proportion of each constituent can be easily determined by the person skilled in the art. Thus for example it is possible to use a racemic mixture of poly(D- and L-lactic acids) or a PLA/PLG mixture at various percentages known to the person skilled in the art. The colloidal synthetic vector according to the invention is preferably prepared from at least one polymer chosen from amongst the poly(α-hydroxy acids). More preferably, the particles according to the invention are free of stabiliser and surfactant so that they are not toxic. A toxic microparticle is understood to be a microparticle including at least one compound capable of causing biological problems, such as disturbances of the metabolism, in the organism which has received the microparticle. Such non-toxic particles can be prepared according to the protocol described in Patent Application WO2005/027871.

According to another embodiment, the colloidal synthetic vector is prepared from at least one natural polymer such as those referred to above The composition according to the invention is useful for stimulating both a cell-mediated response and a humoral response. It is useful both in prophylaxis and therapy and in diagnosis.

Thus the protein substances which are useful for the purposes of the invention and are carried by the synthetic vector can be any protein substances against which an immune response is to be triggered.

An immune response is understood to be a cell-mediated response, a humoral response or both.

A cell-mediated response is understood to be a response mediated by the T-lymphocytes and/or other leucocytes. This response is reflected in the induction of a lytic activity by the cytotoxic T lymphocytes and/or by the production of cytokines by the CD8+ T lymphocytes or by the helper T cells.

A humoral response is understood to be a response mediated by the antibody molecules secreted by the B lymphocytes.

A protein substance is understood to be any protein substance playing the role of antigen after addition to the vectors which are appropriate for the purposes of the invention such as peptides, proteins, protein fragments, polyproteins and glycoproteins, it being understood that the protein fragments have retained the relevant structure.

Antigens are molecules capable of being recognised by an antibody of which they have induced the synthesis by an immune response and containing at least one epitope.

Examples of protein fragments comprise for peptides, polypeptides and epitopes.

Epitopes are peptides comprising between 3 and 15 and generally between 5 and 15 amino acids, consisting of the minimum peptide fragment against which an immune response is triggered.

The synthetic vector has multiple copies of the protein substances. "At least one protein substance" is understood to mean at least several protein substances of the same type. "A type of protein substance" is understood to mean a set of protein substances which trigger the same immune response by production of the same antibodies (i.e. having the same immunity).

The synthetic vector may therefore comprise:
  either protein substances of the same type and therefore constituting antigens associated with the same disease. Thus for example the synthetic vector may comprise as protein substance the protein p24 in the form of native protein and/or mutated protein and/or protein fragment, it being understood that the mutated protein and the fragment have retained their immunity;
  or protein substances of different types and constituting antigens associated with the same disease. Thus for example the synthetic vector may comprise several proteins of the human immunodeficiency virus (HIV) such as the Gag protein, the muted Gag protein which does not have the same immunity, the Tat protein, the Rev protein, the Nef protein, the Env protein;
  or protein substances of different types and constituting antigens associated with different diseases. Thus for example the synthetic vector may comprise at least one type of protein of HIV, such as the p24, Tat, Rev proteins and at least one type of protein of the hepatitis C virus (HCV) such as the proteins NS2, NS3, NS4.

According to one embodiment of the invention, the synthetic vector comprises protein substances of different types and constituting antigens associated with the same disease.

The protein substances may be of several origins such as viral or bacterial origin or of a pathology of non-infectious origin (such as cancer or a metabolic disease).

According to a particular embodiment of the invention, the protein substance is an antigen of viral origin.

When the protein substance is of viral origin, the viruses used are all viruses for which substances capable of an immune response are known.

By way of example, mention may be made without any limitation of herpes viruses, hepatitis viruses such as hepatitis B virus (HBV) or hepatitis C virus (HCV), papilloma viruses (HPV), human immunodeficiency viruses (HIV), such as HIV-1 and HIV-2, different strains of the human influenza and avian influenza viruses.

The nucleic sequences of the viruses which are appropriate for the purposes of the invention, as well as the proteins coded by the said sequences are widely known to the person skilled in the art and are available for example in databases such as GenBank.

Thus for example the HIV virus has genes which code for structural proteins of the virus. The Gag gene codes for the protein which forms the core of the virion, including the p24 antigen. The Pol gene codes for the enzymes responsible for the reverse transcription (reverse transcriptase), cleavage (protease) and integration (integrase). The Env gene codes for envelope glycoproteins. It contains other genes (Tat, Rev, Nef, Vif, Vpr and Vpu (HIV-1) or Vpx (HIV-2) which code for proteins involved in the regulation of the expression of the genes of the virus (regulating proteins). The HIV genome also comprises the 5' and 3' LTRs (long terminal repeats) which comprise regulating elements involved in the expression of the genes of the virus.

According to one embodiment of the invention, the protein substance used in the method according to the invention is a protein of the HIV virus. As an example of an antigen of the HIV virus mention may be made of regulating proteins or the Gag protein or the Env glycoprotein, the preferred regulating proteins being the Tat, Rev or Nef protein.

In the case of the HCV, the 5' end of its genome corresponds to a non-translated region adjacent to the genes which code for the structural proteins, the core protein of the nucleocapsid, the two envelope glycoproteins, E1 and E2, and a small protein known as p7. The 5' non-translated region and the core gene are relatively well preserved in the different genotypes. The envelope proteins E1 and E2 are coded by regions which are more variable from one isolate to another. The p7 protein is an extremely hydrophobic protein which would constitute an ion channel. The 3' end of the HCV genome contains the genes which code for the non-structural proteins (NS2, NS3, NS4, NS5) and for a non-coding 3' region having a well preserved domain (Major M E, Feinstone S M, Hepatology, June 1997, 25(6): 1527-1538).

The non-structural protein NS3 of the HCV is a protein of 630 amino acids which comprises two distinct structural domains: an N-terminal domain of 81 amino acids, endowed with an active serine protease activity which intervenes in the maturation of the viral protein (domain called NS3 protease), and a C-terminal domain of 549 amino acids, comprising a helicase activity associated with an NTP ase activity which plays a part in the reproduction of the viral genome (domain called NS3 helicase). This protein NS3 is relatively well preserved amongst the different genotypes of the virus, such that this protein constitutes a "candidate vaccine" antigen of choice.

According to another embodiment of the invention, the protein substance is an antigen associated with tumours.

For certain tumours express antigens which are potentially recognised by the CD8+ T lymphocytes even if they do not have their origin in an intense immune response. These are tumour-associated antigens (TAA) or tumour markers (Houghton A N, 1994, J Exp Med 180:10). By improving the presentation of the TAAs to the immune system it is possible to render them more immunogenic, thus the TAAs can serve as a base for the development of anti-cancer vaccines in the form of a recombinant protein or a synthetic peptide.

In order to test the new immunotherapy strategies which aim to increase the knowledge of TAAs, Wang et al have developed an experimental model in mice (1995, Journal of Immunology, 154: 4685-4692). The tumour line CT26.WT, genetic base BALB/c, was transfected by the lacZ gene of *Escherichia coli* which codes for the enzyme beta-galactosidase in order to create the line CT26.CL25. The two lines are lethal in mice and their growth kinetics are similar. Administered in mice, the line CT26.CL25 is the origin of the formation of tumours which can be slowed down or indeed inhibited in the presence of an immune response against beta-galactosidase which constitutes a model TAA.

The protein substances appropriate for the purposes of the invention can be obtained by genetic engineering techniques which include the steps of:
  culture of a microorganism or eukarytic cells transformed with the aid of a nucleotide sequence which codes for the relevant protein substance, and
  recovery of the said protein substance produced by the said microorganism or the said eukarytic cells.

These techniques are well known to the person skilled in the art. For further details in this connection, reference may be made to the following work: Recombinant DNA Technology I, Editors Ales Prokop, Raskesh K Bajpai: Annals of the New York Academy of Sciences, Volume 646, 1991.

When the relevant protein substances are small in size, they can also be prepared by conventional peptide syntheses which are well known to the person skilled in the art.

The protein substance is combined with the colloidal vectors according to techniques which are known to the person skilled in the art, such as inclusion or bonding on the surface. As an example of the inclusion of the protein substance in the colloidal synthetic vector, mention may be made of encapsulation (Tamber H. et al, 2005, Adv Drug Deliv Rev, 57(3); 357-76).

As an example of bonding of the colloidal substance to the colloidal synthetic vector, mention may be made of adsorption, as described in Patent Application WO2005/027871, or covalent grafting involving the formation of a chemical bond between a reactive group of the colloidal vector and another of the protein substance in a manner described for example in "Protein immobilization Fundamentals and Applications R. F. Taylor Ed, Marcel Dekker Inc., New York, 1991.

According to a particular embodiment, the protein substances are added to the synthetic vectors by bonding and more preferably by adsorption, such as for example by mixing the microparticles with the protein substances and incubating them whilst stirring, for example at ambient temperature or at 37° C.

The composition according to the invention also comprises a viral vector.

The viral vector comprises at least one nucleotide sequence which codes for a protein substance corresponding to at least one protein substance of the synthetic vector.

"Protein substance of the viral vector corresponding to at least one protein substance of the synthetic vector" is understood to mean that the protein substance of the viral vector constitutes an antigen associated with the same disease as the protein substance of the synthetic vector, regardless of whether it is the same type or a different type, as indicated above. When the protein substances are of a different type they must have at least one epitope in common, such as for example the Gag and p24 proteins.

Thus the genome of the viral vector is modified so as to insert one or several nucleotide sequences which code for one or several protein substances constituting antigens of the same disease or of different diseases. Amongst these protein substances at least one corresponds to a protein substance of the synthetic vector, these protein substances constituting antigens associated with the same disease.

According to a preferred embodiment, the viral vector comprises a nucleotide sequence which codes for a protein of HIV.

Apart from the nucleotide sequence or sequences coding for at least one protein substance constituting an antigen associated with the same disease as the protein substance of the synthetic vector, the viral vector also comprises the means necessary for the expression of the said protein substance.

"Means necessary for the expression of a protein substance" are understood to mean any means which enable the protein substance to be obtained, such as in particular a promoter, a transcription terminator, an origin of replication and preferably a selection marker.

The means necessary for the expression of a protein substance are operably linked to the nucleic acid sequence which codes for the said substance. "Operably linked" is understood to mean a juxtaposition of the said elements necessary for expression and of the gene which codes for the protein substance, which are in a relation which enables them to function in the expected manner. For example, additional bases may exist between the promoter and the relevant gene as long as their functional relation is maintained.

The means necessary for the expression of the protein substance may be homologous means, that is to say means included in the genome of the vector which is used, or they may be heterologous. In this latter case the said means are cloned with the relevant protein to be expressed.

Examples of heterologous promoters comprise (i) viral promoters such as the promoter SV40 (simian virus 40), the promoter of the thymidine kinase gene of the herpes simplex virus (TK-HSV-1), the LTR of the Rous sarcoma virus (RSV), the intermediate early promoter of the human cytomegalovirus (CMV) and the adenoviral major late promoter (MLP), as well as (ii) any cellular promoter which controls the transcription of the genes which code for proteins in higher eukaryotes, such as the promoter of the constitutive phosphoglycerate kinase (PGK) gene (Adra et al, 1987, Gene, 60: 65-74), the promoter of the specific genes of liver alphal antitrypsin and FIX and the specific promoter SM22 of soft muscle cells (Moessler et al, 1996, Development, 122: 2415-2425).

The said sequences contained in the viral vector can be linked directly to one another under the control of one single promoter and/or one single expression regulating element, or they can be separated by each being dependent upon independent promoters and/or expression regulators which may be identical or different.

By way of viral vectors which are suitable for the purposes of the invention, mention may be made for example of the viral vectors of the adenovirus, poxvirus, baculovirus, herpes virus, togavirus, retrovirus type.

Adenoviruses have been detected in numerous animal species. They do not integrate and are not very pathogenic. They are capable of infecting a variety of cell types, dividing cells and resting cells. They have a natural tropism for bronchial epitheliums. Moreover, they have been used as live enteric vaccines for a number of years with an excellent safety record. Finally, they can be easily grown and purified in large quantities. Due to these characteristics adenoviruses are particularly appropriate for use as expression vectors and in particular as gene therapy vectors for the purposes of therapy and vaccination.

According to a preferred embodiment, the vector according to the invention is an adenovirus.

Examples of adenoviruses to be used in the present invention may be derived from any source of human or animal origin, in particular of canine origin (for example CAV-1 or CAV-2; GenBank reference CAV1GENOM and CAV77082 respectively), of avian origin (GenBank reference AAVEDSDNA), of bovine origin (such as BAV3, Seshidhar Reddy et al, 1998, J. Virol., 72:1394-1402), of ovine, feline or porcine origin, of simian origin, or one of their hybrids. Any serotype may be used. However, the adenoviruses of human origin are preferred and in particular the adenovirus 5 (Ad5).

In general, the viruses referred to are available in the ATCC collections and have been the subject of numerous publications describing their sequences, their organisation and their biology, which enables the person skilled in the art to apply them easily. For example, the sequence of the adenovirus type 5 is described in the GenBank database (M73260 and M29978) and is incorporated herein by reference.

The genome of adenoviruses consists of a linear double-strand DNA molecule of approximately 36 kb carrying more than approximately 30 genes necessary for terminating the viral cycle. There are 4 early genes distributed in the genome of the adenovirus (E1 to E4). The regions E1, E2 and E4 are essential for the viral replication. The region E3 is considered as a non-essential region based on the observation that mutant viruses appear naturally or hybrid viruses which have lost this region E3 continue to replicate like viruses of the wild type in cultured cells (Kelly and Lewis, 1973, J. Virol., 12: 643-652). The majority of late genes (L1 to L5) code for the structural proteins which form the viral capsid. They at least partially overlap the first transcription motifs and are transcribed on the basis of single promoter (MLP for "major late promoter"). Moreover, the adenoviral genome carries at the two ends cis-action regions which are essential for the DNA replication respectively the inverted repeat motifs 5' and 3' (ITRs for "inverted terminal repeats") and a packaging sequence.

The adenoviruses currently used in the gene therapy protocols are devoid of the majority of region E1, which makes the viruses deficient at the replication level in order to prevent their dissemination in the environment and in the host organism. Moreover, the majority of adenoviruses are also devoid of region E3 in order to increase their cloning capacity. The feasibility of gene transfer using these vectors has been demonstrated in a variety of tissues in vivo (see for example Yei et al, 1994, Hum. Gen. Ther., 5: 731-744; Dai et al, 1995, Proc. Natl. Acad. Sci. USA, 92: 1401-1405; U.S. Pat. Nos. 6,099,831; and 6,013,638).

Another expression vector which is particularly appropriate for the purposes of the invention is a poxvirus, which constitutes another embodiment of the invention.

Poxviruses constitute a group of complex enveloped viruses which are distinguished principally by their unusual morphology, their large DNA genome and their cytoplasmic replication site. The genome of several elements of the poxviridiae, comprising the viral strain of the Copenhagen vaccinia (VV) (Goebel et al, 1990, Virol. 179: 247-266 and 517-563) and the strain of the Modified Vaccinia Virus Ankara (MVA) (Antoine et al, 1998, Virol., 244: 635-396), has been mapped and sequenced. The strain VV has a double-strand DNA genome of approximately 192 kb which codes for approximately 200 proteins of which approximately 100 are involved in the assembly of the virus. The strain MVA is a highly attenuated strain of the vaccinia virus, generated by more than 500 serial passages of the Ankara strain of the vaccinia virus (CVA) on chicken embryo fibroblasts (Mayr et al, 1975, Infection, 3: 6-16). The virus MVA has been deposited at the Collection Nationale de Cultures de Microorganismes (CNCM) under the number 1-721. The determination of the complete sequence of the genome of MVA and the comparison with that of VV enables precise identification of the alterations which have occurred in the viral genome and the definition of seven deletions (I to VII) and numerous mutations leading to fragmented open reading frames (Antoine et al, 1998, Virology, 244: 365-396).

Other examples of poxviruses which are appropriate for the purposes of the invention comprise canarypox, fowlpox, cowpox, entomopox, monkeypox, swinepox and penguinpox.

Poxvirus occurs in two morphologically distinct forms, known as intracellular mature virus (IMV) and extracellular enveloped virus (EEV).

The poxvirus used for the purposes of the invention is preferably a modified vaccinia virus Ankara.

The methods of suppression and insertion of DNA sequences in expression vectors are widely known by the person skilled in the art and consist in particular of steps of enzymatic digestion and ligation. The nucleotide sequence inserted into the viral vector preferably codes for a protein of the HIV virus.

The compositions based on vectors according to the invention are particularly effective for inhibiting, preventing and treating a disease for which the protein substance of the composition constitutes an antigen, such as an infection by a virus. They are therefore particularly useful for the preparation of a medicament, in particular a vaccine, which may be therapeutic or prophylactic.

Thus the invention also relates to a method of prophylactic or therapeutic treatment, in particular vaccination, comprising the administration to a patient of an effective dose of the composition according to the invention.

The pharmaceutical compositions according to the invention are appropriate for oral, sublingual, subcutaneous, intramuscular, intravenous, topical, local, intratracheal, intranasal, transdermal, rectal, vaginal, intraocular, intraauricular administration, and the said active principle can be administered in unitary administration form.

The unitary administration forms may be for example tablets, capsules, granules, powders, injectable oral solutions or suspensions, transdermal patches, sublingual, buccal, intratracheal, intraocular, intranasal, intraauricular forms of administration, forms of administration by inhalation, topical forms of administration such as rectal or vaginal, transdermal, subcutaneous, intramuscular or intravenous forms of administration, or implants. For topical administration creams, gels, ointments, lotions or collyria may be envisaged.

These Galenic forms are prepared by the usual methods in the fields in question.

The said unitary forms are dosed in order to enable daily administration of 0.001 to 10 mg of active principle per kg of body weight depending upon the Galenic fat u.

There may be particular cases where higher or lower dosages are appropriate; such dosages do not depart from the scope of the invention. According to usual practice, the appropriate dosage for each patient is determined by the doctor according to the mode of administration, the weight and the response of the patient.

The quantity and the nature of the excipient can be easily determined by the person skilled in the art. They are chosen as a function of the pharmaceutical form and the mode of administration which are required.

The composition according to the invention can be contained in a pharmaceutical kit. The administration of the composition according to the invention may be simultaneous, separate or staggered.

Simultaneous administration is understood to mean administration of the composition at the same time and at the same location.

Staggered administration is understood to mean the administration of the viral vector or the synthetic vector at different times. The interval between each administration may extend from a few minutes to several years, preferably from several weeks to several months and more preferably it may be 3 or 4 weeks.

Separate administration is understood to mean the administration of the viral vector and the synthetic vector at different locations on the body. The viral vector and the synthetic vector may be in the same excipient or preferably in appropriate different excipients.

The composition according to the invention is preferably administered in a staggered manner. More preferably the synthetic vector is administered before the viral vector.

Thus according to an embodiment of the invention, the composition according to the invention comprises:
i) a prime constituent consisting of the colloidal synthetic bioresorbable vector comprising at least one protein substance and
ii) a boost constituent consisting of the viral vector comprising at least one nucleotide sequence which codes for a protein substance corresponding to at least one protein substance of the synthetic vector.

In addition to a therapeutic and prophylactic application, the invention also has a diagnostic application. Thus the invention also relates to the use of the composition according to the invention for the diagnosis in vitro of the pathological state for which the protein substance or substances of the synthetic vector and of the synthetic vector constitute antigens, and in particular of a viral infection or a cancer.

The present invention will be better understood with the aid of the following examples which are given solely by way of illustration and are not limiting, and also with the aid of the appended FIGS. 1 to 20, in which.

Figure 13:
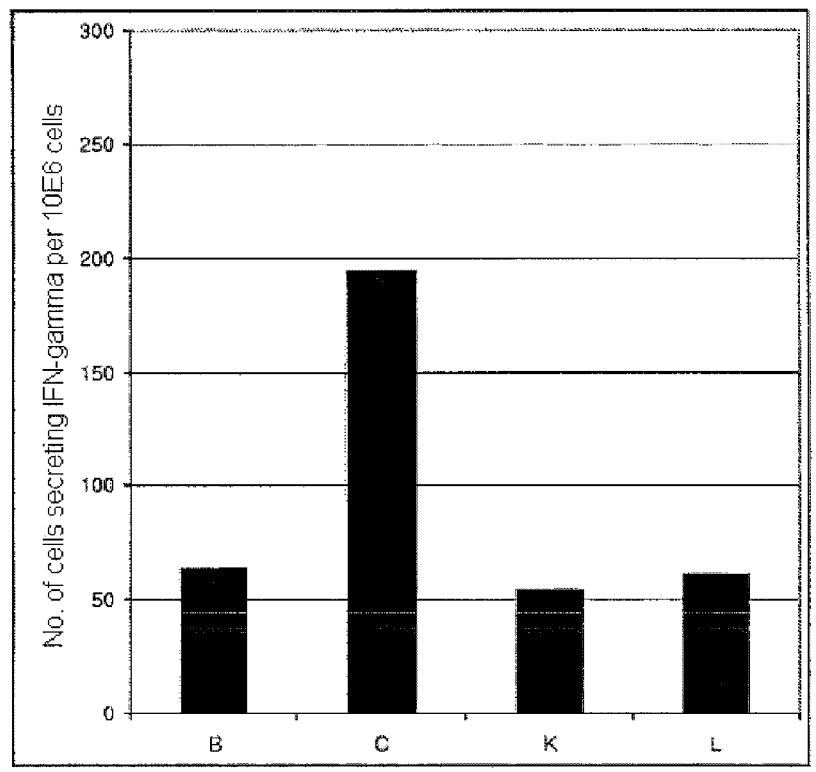

FIG. 13 compares the specific ELISPOT IFN-γ responses of the peptide Gag AMQ after immunisation with different vaccine compositions including the compositions which comprise PLA/p24 and MVA Gag or comprise alum/p24 and MVA Gag.

Figure 14:
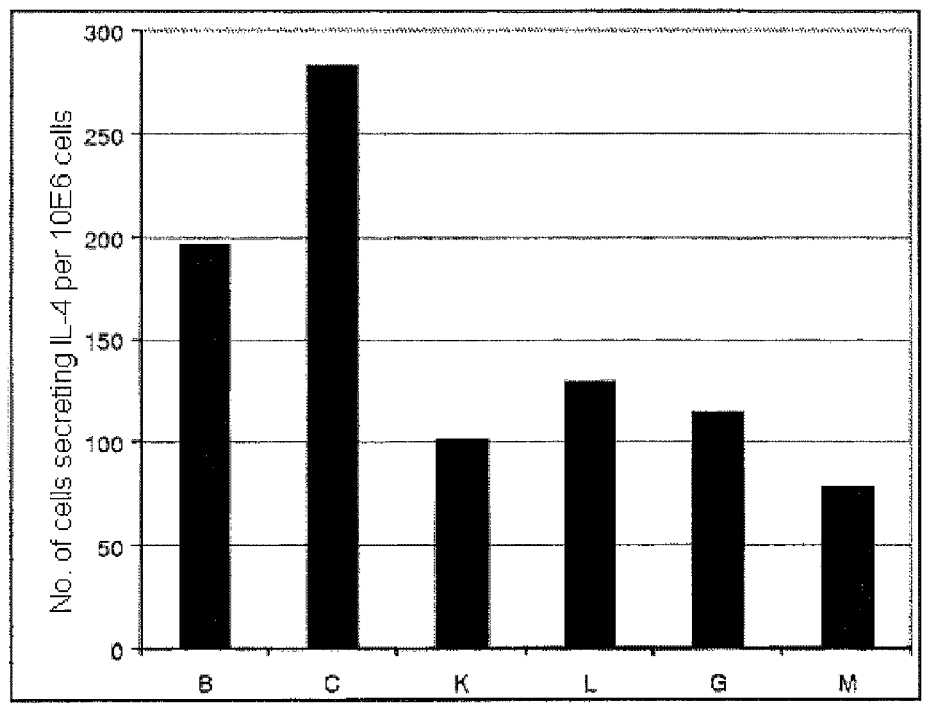

FIG. 14 compares the specific ELISPOT IL-4 responses of the protein p24 after immunisation with different vaccine compositions including the compositions which comprise PLA/p24 and MVA Gag or comprise alum/p24 and MVA Gag.

Figure 15:
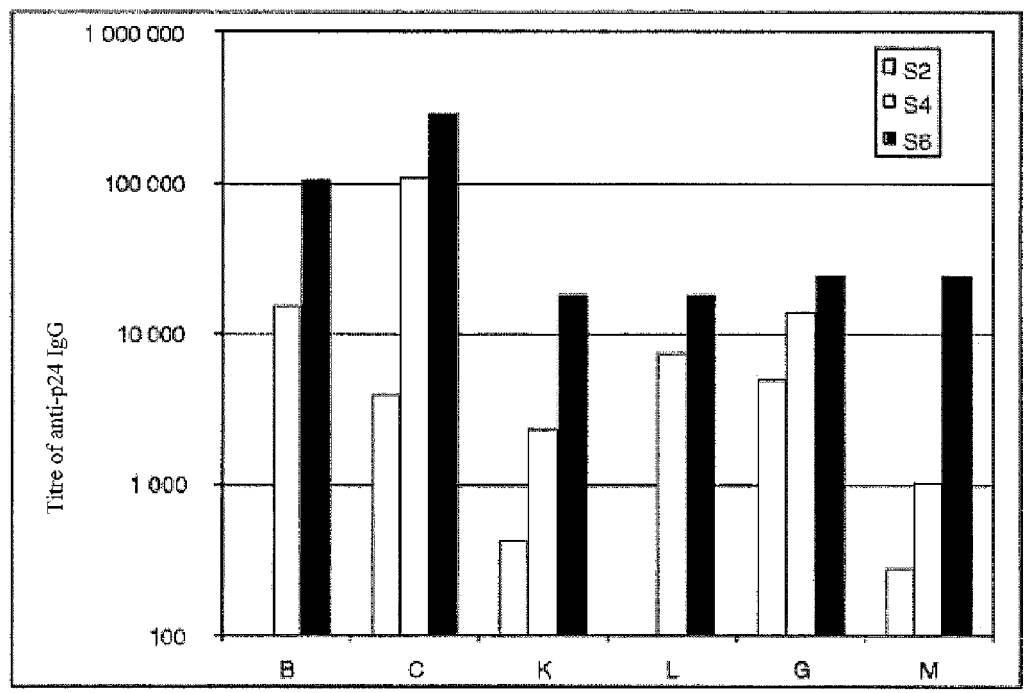

FIG. 15 compares the appearance kinetics of the specific humoral responses of the protein p24 after immunisation with different vaccine compositions including the compositions which comprise PLA/p24 and MVA Gag or comprise alum/p24 and MVA Gag.

Figure 16:
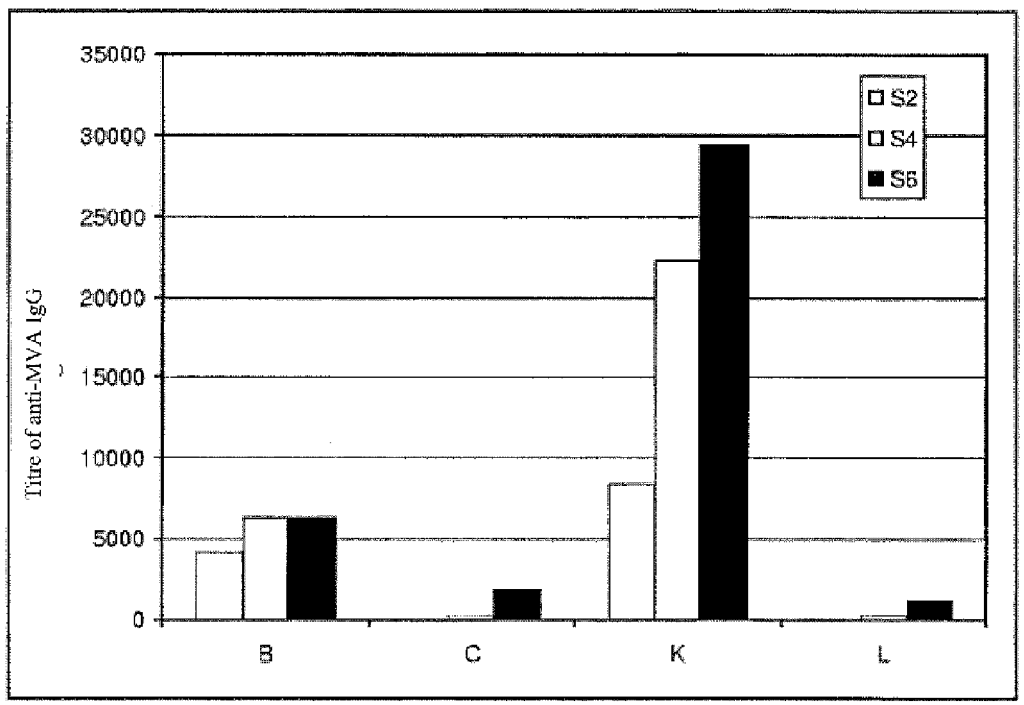

FIG. 16 compares the appearance kinetics of the specific humoral responses of the MVA virus after immunisation with different vaccine compositions including the compositions which comprise PLA/p24 and MVA Gag or comprise alum/p24 and MVA Gag.

Figure 17:
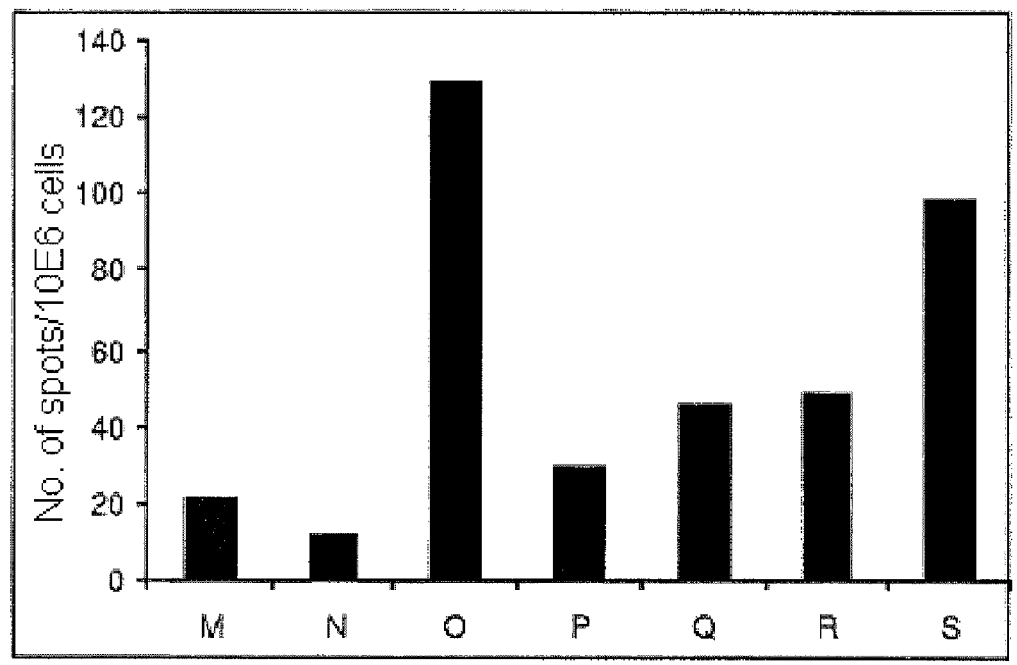

FIG. 17 shows the specific ELISPOT IFN-γ responses of the peptide beta-gal TPH after immunisation of mice with different vaccine compositions including the compositions according to the invention which comprise the synthetic vector PLA-beta-gal and the viral vector MVA beta-gal.

Figure 18:
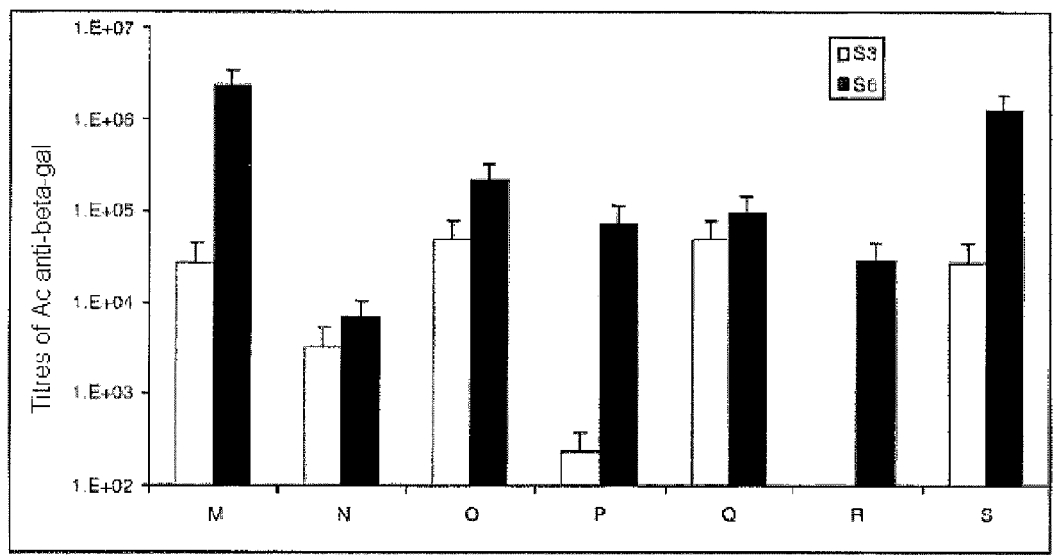

FIG. 18 compares the appearance kinetics of the specific humoral responses of the beta-gal after immunisation of mice with different vaccine compositions including the compositions according to the invention which comprise the synthetic vector PLA-beta-gal and the viral vector MVA beta-gal.

Figure 19:
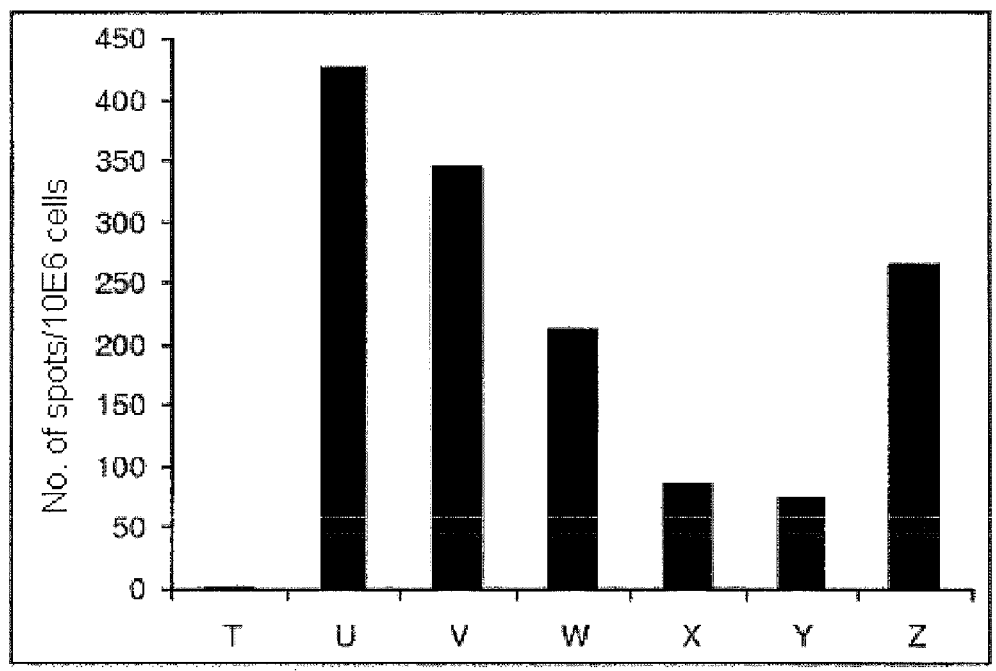

FIG. 19 shows the specific ELISPOT IFN-γ responses of the peptide p24 AMQ after immunisation of mice with different vaccine compositions including the compositions according to the invention which comprise the synthetic vector CPL-P24 and the viral vector MVA Gag.

Figure 20:
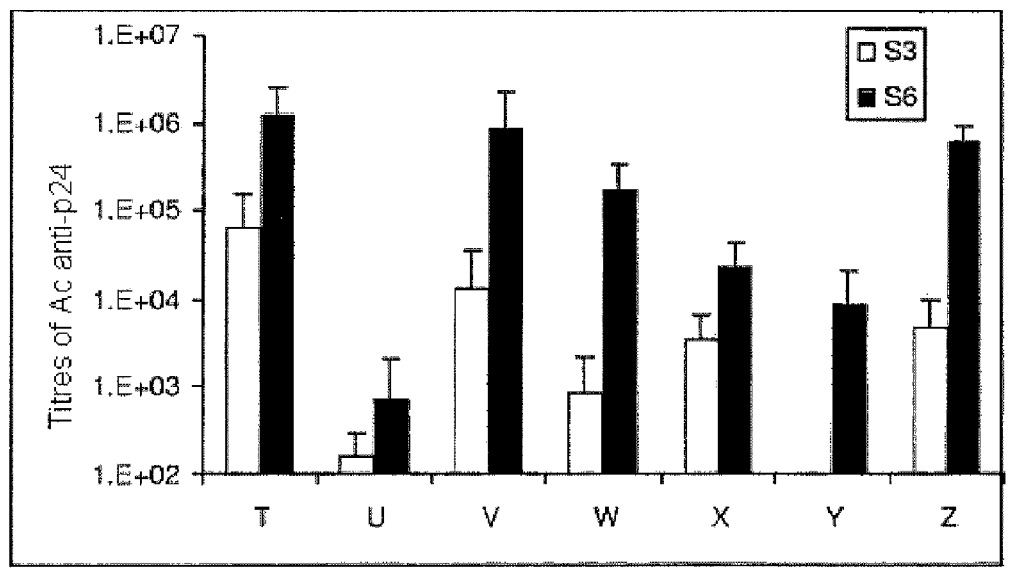

FIG. 20 compares the appearance kinetics of the specific humoral responses of the peptide p24 AMQ after immunisation of mice with different vaccine compositions including the compositions according to the invention which comprise the synthetic vector CPL-P24 and the viral vector MVA Gag.

EXAMPLE 1

Immunisation of Mice with a Vaccine Composition According to the Invention

The vaccine composition used comprises a synthetic vector based on microparticles of poly(D,L-lactic acid) combined with protein p24 (referred to hereafter as PLA/p24) and a viral vector MVA comprising the Gag sequence of SEQ ID No 1 (referred to hereafter as MVA Gag virus).

1. Animal Model

The immunisation experiments were carried out in female BALB/c (H-2K$^d$) mice aged from 6 to 8 weeks at the time of the first immunisation.

2. Immunogens Administered

In this series of experiments the following immunogens were used alone or in combination:

microparticles PLA/p24 prepared according the solvent displacement and adsorption procedure of Patent Application WO2005/027871.

the virus MVA Gag (modified vaccinia virus Ankara, attenuated vaccinia virus, Ankara strain) which is recombinant for the Gag gene of the HIV-1 virus, coding for the protein p24. The recombinant virus was constructed at Transgene from the wild strain (MVATGN33) as described in Antoine G. et al, 1998, "The complete genomic sequence of the modified vaccinia Ankara strain; comparison with other orthopoxviruses", Virology, 244: 365-396. This recombinant virus was then produced and purified as follows: the MVA is replicated on chicken embryo cells. After 48 to 72 hours of infection the cells are harvested, then lysed by freezing/thawing and by sonication. The lysate is purified/concentrated by 2 saccharose pads optionally followed by 2 saccharose gradients. For more precise details reference may be made to the book "Current Protocols in Molecular Biology", Volume 2, Chapter 16.16, editors Ausubel F M, Brent R, Kigston R E, Moore D D, Seidman J G, Smith J A, Struhl K, John Wiley & Sons, Inc., New York, 3 volumes.

the wild MVA virus MVATGN33. This is a negative control which serves to measure whether the viral vector induces a non-specific immune response during the immunisations.

Gag DNA. The Gag gene (from SEQ ID No. 1) was cloned in the eukaryotic expression plasmid phCMV (contains the intermediate/early promoter of the human cytomegalovirus and splicing and polyadenylation signals from the rabbit beta-globin gene (Y K Yee et al, 1994, Proc Natl Acad Sci USA, 91(20):9564-9568)). DNA preparations without endotoxins and in a large quantity have been produced using the Gigaprep endotoxin-free kit from Macherey-Nagel. The DNA serves as positive control, since it is known that in mice the intramuscular administration of naked DNA makes it possible to induce a good cytotoxic response (CTL).

3. Immunisations

Experiment 1

35 mice received 2 doses of the immunogens described in point 2 above at 0 and 3 weeks. The vaccine compositions received by each group of mice are indicated in Table 1 below. All the injections were carried out subcutaneously except for the DNA which was administered by the intramuscular route.

TABLE 1

| Dose 1st injection Week 0 | Dose 2nd injection Week 3 | Number of mice |
| --- | --- | --- |
| MVA Gag 10$^7$ pfu | MVA Gag 10$^7$ pfu | 5 |
| MVA Gag 10$^7$ pfu | PLA/p24 40 µg | 5 |
| PLA/p24 40 µg | MVA Gag 10$^7$ pfu | 5 |
| PLA/p24 40 µg | PLA/p24 40 µg | 5 |
| wild MVA 10$^7$ pfu | wild MVA 10$^7$ pfu | 5 |
| DNA Gag 10 µg (IM) | PLA/p24 40 µg | 5 |
| PLA/p24 40 µg | DNA Gag 10 µg (IM) | 5 | pfu = plaque forming units, this is the unit of measurement of the dose of MVA used. The viral titre is expressed in pfu according to the technique of dosage of the viral stock used, as indicated in Current Protocols in Molecular Biology, see above.

The animals were sacrificed 6 weeks after the first injection and the blood and the spleen were removed for immunological analyses.

Experiment 2

In this experiment the number of injections was increased.

30 mice received 2 or 3 doses of the immunogens described in point 2 above at 0, 3 and 6 weeks. The vaccine compositions received by each group of mice are indicated in Table 2 below. All the injections were carried out subcutaneously.

TABLE 2

| 1st injection Week 0 | 2nd injection Week 3 | 3rd injection Week 6 | Number of mice |
| --- | --- | --- | --- |
| MVA Gag 10$^7$ pfu | MVA Gag 10$^7$ pfu | | 5 |
| MVA Gag 10$^7$ pfu | MVA Gag 10$^7$ pfu | MVA Gag 10$^7$ pfu | 5 |
| MVA Gag 10$^7$ pfu | PLA/p24 40 µg | | 5 |
| MVA Gag 10$^7$ pfu | PLA/p24 40 µg | PLA/p24 40 µg | 5 |
| PLA/p24 40 µg | MVA Gag 10$^7$ pfu | | 5 |
| wild MVA 10$^7$ pfu | wild MVA 10$^7$ pfu | wild MVA 10$^7$ pfu | 5 |

The animals were sacrificed 3 weeks after the last injection and the blood and the spleen were removed for immunological analyses.

Experiment 3

30 mice received 2 or 3 doses of the immunogens described in point 2 above at 0, 3 and 6 weeks. The vaccine compositions received by each group of mice are indicated in Table 3 below. All the injections were carried out subcutaneously.

TABLE 3

| 1st injection Week 0 | 2nd injection Week 3 | 3rd injection Week 6 | Number of mice |
| --- | --- | --- | --- |
| MVA Gag 10$^7$ pfu | PLA/p24 40 µg | | 5 |
| MVA Gag 10$^7$ pfu | PLA/p24 40 µg | PLA/p24 40 µg | 5 |
| PLA/p24 40 µg | MVA Gag 10$^7$ pfu | | 5 |
| PLA/p24 40 µg | MVA Gag 10$^7$ pfu | PLA/p24 40 µg | 5 |

TABLE 3-continued

| 1st injection<br>Week 0 | 2nd injection<br>Week 3 | 3rd injection<br>Week 6 | Number<br>of mice |
|---|---|---|---|
| PLA/p24 40 µg | PLA/p24 40 µg |  | 5 |
| PLA/p24 40 µg | PLA/p24 40 µg | PLA/p24 40 µg | 5 |

The animals were sacrificed 3 weeks after the last injection and the blood and the spleen were removed for immunological analyses.

4. Immunological Analyses

The humoral response and the cell response were researched as follows:

Humoral response: blood was taken from the mice before they were sacrificed. The presence of anti-p24 antibodies was determined by ELISA. The protein p24 (produced with *Escherichia coli* and purified by metal chelate affinity chromatography according to Cheynet V. et al, 1993, Protein Expr Purif, 4(5): 367-72) was used in capture and the specific antibodies present in the serum were revealed by a polyclonal anti-mouse antibody as detection antibody which is an Affinipure goat anti-mouse IgG antibody conjugated with horseradish peroxidase (H+L, Jackson Immunoresearch, Cat no 115-035-062). The titre is the inverse of the dilution for which an absorbency of 0.1 OD unit is obtained with the ELISA protocol used.

Cell response: after sacrifice of the mice, the spleens were removed in a sterile manner in order to prepare a cell suspension. The following analyses were carried out on the cell suspensions obtained, each mouse having been analysed individually or in a pool when the quantity of cells was not sufficient for individual analysis.

(i) CTL test: The cell suspension was cultured in the presence of a peptide of the protein p24 of 9-mer (AMQM-LKETI—SEQ ID No. 2) which corresponds to an immunodominant H-2K-restricted CTL epitope, and IL-2. Five days later, the effector population was restimulated by irradiated naïve cells charged with the peptide. The cytotoxic effector population was harvested at the end of the 7th day and the CTL activity was measured using the cells P815 (ATCC TIB-64) marked with $^{51}Cr$ as targets.

(ii) ELISPOT: ELISPOT makes it possible to determine the number of cells secreting a given cytokine in response to a specific stimulus. We are interested in the cytokines IFN-γ of type Th1 and IL-4 of type Th2. The cell suspensions obtained from the spleens were restimulated in vitro by the peptide AMQMLKETI for 20 hours in order to analyse the responses of type CD8. The cell suspensions obtained from the spleens were restimulated in vitro by the protein p24 (without endotoxins) for 42 hours in order to analyse the responses of type CD4.

The 96-well ELISPOT plates with PVDF membranes (Multiscreen IP, Millipore) were coated by an anti-IFN-? or anti-IL-4 antibody. During the restimulation the suspensions of splenocytes were incubated in these plates in such a way as to capture the cytokines secreted by each cell. The spots corresponding to each cell secreting the relevant cytokine were revealed by a specific biotinylated detection antibody of the relevant cytokine.

iii) Secretion of cytokines: The splenocytes were stimulated for 3 days in complete culture medium (culture medium: alpha minimal essential medium (aMEM) containing 10% foetal calf serum, 10 mM HEPES, $5 \times 10^{-5}$ M β-mercaptoethanol, 4 nM L-glutamine, 80 U/ml penicillin, 80 mg/ml streptomycin, non-essential amino acids 1× (cat. no. 11140-035), sodium pyruvate 1× (cat no. 11360-039) (constituents of Invitrogen, Cergy Pointoise, France)) in the presence or absence of the relevant p24 antigen, then the cytokines secreted in the culture supernatant were dosed by the mouse kit FlowCytomix Th1/Th2 10plex from Bender Medsystems (cat no. BMS720FF).

5. Results 5.1 the CTL Response

Table 4 below recapitulates the results obtained during the 3 successive experiments:

TABLE 4

| Code | Vaccine composition | Mice analysed in pool (Exp 1, n = 5) | Frequency of mice with CTL response Number of positive mice/ number of mice analysed individually |
|---|---|---|---|
| A | MVA Gag + MVA Gag | Negative pool | 0/5 |
| A' | MVA Gag + MVA Gag + MVA Gag |  | 1/5 |
| B | MVA Gag + PLA/p24 | Negative pool | 1/10 |
| B' | MVA Gag + PLA/p24 + PLA/p24 |  | 3/10 |
| C | PLA/p24 + MVA Gag | Positive pool | 2/10 |
| C' | PLA/p24 + MVA Gag + PLA/p24 |  | 1/5 |
| F | DNA Gag + PLA/p24 | Positive pool | Not carried out |
| G | PLA/p24 + DNA Gag | Positive pool | Not carried out |
| D | PLA/p24 + PLA/p24 | Negative pool | 0/5 |
| D' | PLA/p24 + PLA/p24 + PLA/p24 |  | 0/5 |
| E | MVA + wild MVA | Negative pool | Not carried out |
| E' | MVA + MVA + wild MVA |  | 0/5 |

Figure 1:
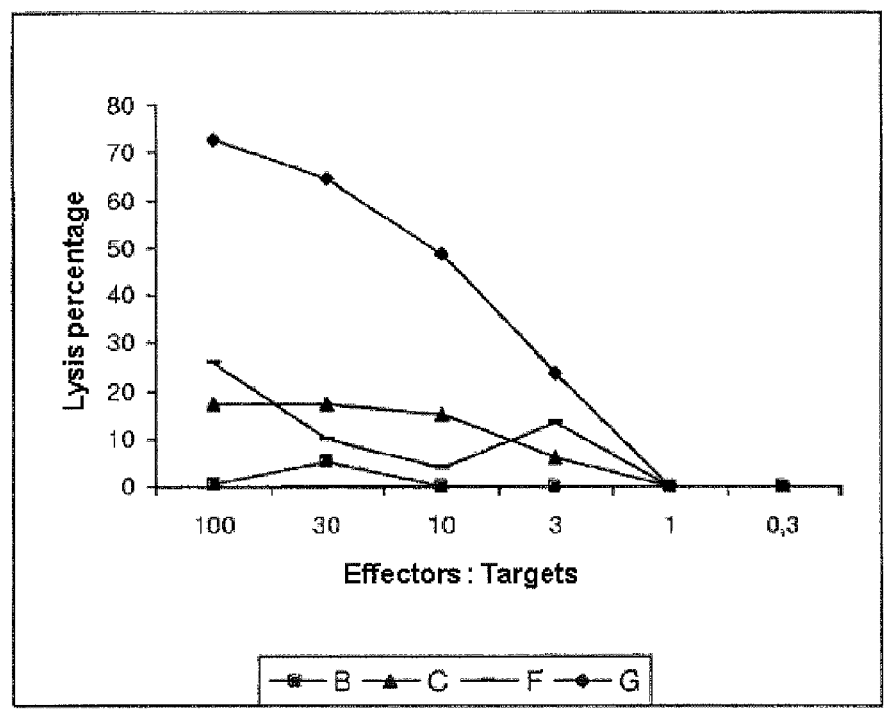
FIG. 1 shows the CTL responses during the immunisation experiment No. 1 with different vaccine compositions including the compositions according to the invention which comprise a synthetic vector based on microparticles of poly(D,L-lactic acid) combined with protein p24 (referred to hereafter as PLA/p24) and a viral vector MVA comprising the Gag sequence (referred to hereafter as MVA Gag virus).

FIG. 1 shows the CTL responses obtained during the immunisation experiment No. 1. Each group consists of 5 mice, the spleens were pooled before the CTL dosage was carried out. Since the non-specific stimulation (without peptide) in all the groups was 0, this is not shown. Likewise, since the CTL responses obtained with the compositions A, D and E were 0, they are not shown. The X axis corresponds to the ratio of effector cells (CTL) to target cells (to be lysed). The Y axis corresponds to the mean lysis percentage.

The CTL responses induced are of low intensity with all the immunogens used (MVA, PLA or combinations), with the exception of the group G of Experiment 1 which received DNA last (FIG. 1). The induction of CTL in the DNA groups is normal: the DNA is optimised for this purpose, it is a positive control in mice but does not work so well in primates.

Even if the responses remain low, the groups containing both MVA and PLA give better CTL responses than the groups which received MVA alone or PLA alone.

When 2 injections were given, in the groups which received MVA twice or PLA twice there is no CTL detected during the retained sacrifice (A and D), whilst in the groups which received both PLA and MVA (B and C) there is a low frequency of CTL. The order of injection also plays a part: PLA+MVA (C) gives better results than MVA+PLA (B).

When 3 injections were given, the frequency of induction of the responses still remains low. The CTL responses are not improved by comparison with two injections. The vaccine strategy using MVA necessitates 3 injections in order to give the same results as the combinations of PLA and MVA.

5.2 the ELISPOT IFN-γ Response Against the Gag Peptide AMQ

Figure 2:
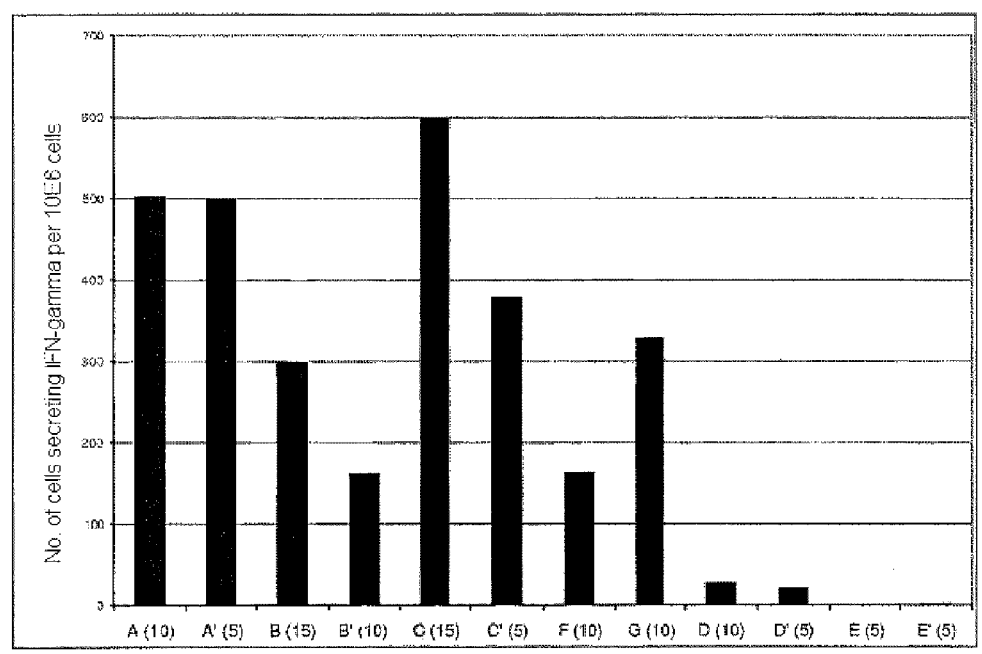
FIG. 2 shows the specific ELISPOT IFN-γ responses of the Gag AMQ peptide during the 3 immunisation experiments with different vaccine compositions including the compositions according to the invention which comprise the synthetic vector PLA/p24 and the viral vector MVA Gag.

FIG. 2 shows the specific ELISPOT IFN-γ responses of the Gag peptide AMQ. All the animals immunised during the 3 successive experiments were included in the analysis. For each vaccine composition the number of animals which received this composition is indicated in brackets. The Y axis shows the mean number of cells secreting IFN-γ in a specific manner in response to a stimulation for 18 hours by the Gag peptide AMQ on a million stimulated cells. This response was determined individually for each mouse. The number presented on this graph corresponds to the calculated mean from all the mice of a group (n=5, 10 or 15 depending upon the groups).

The gamma or type II interferon is also called immune interferon because it is secreted by the type CD4+ T lymphocytes, by the type CD8+ T lymphocytes and the NK cells. It protects the cells against viral infections. It stimulates the phagocytic activity of macrophages, enabling them to kill the tumour cells. It stimulates the maturation of the T and B lymphocytes and increases the production of antibodies. It increases the expression of class I and II HLA molecules by the macrophages. It is a type Th1 cytokine.

It is possible to classify the vaccine compositions into several categories as a function of the ELISPOT IFN-γ responses obtained. The best responses are induced by the compositions PLA+MVA (C) and MVA+MVA (A). In these cases the third injection either does not provide any improvement (composition MVA+MVA) (A') or it can decrease the response observed (composition PLA+MVA) (C'). The compositions MVA+PLA (B and B') and DNA+PLA (F) enable intermediate intensity responses to be generated, whilst the strategy using only PLA (D and D') only induces low responses Thus we have been able to show that the vaccine composition PLA+MVA (C) was at least as good as, if not better than the combination MVA+MVA (A) for inducing a secretion of specific IFN-γ of the peptide AMQ.

5.3 the ELISPOT IFN-γ Response Against the Protein p24

Figure 3:
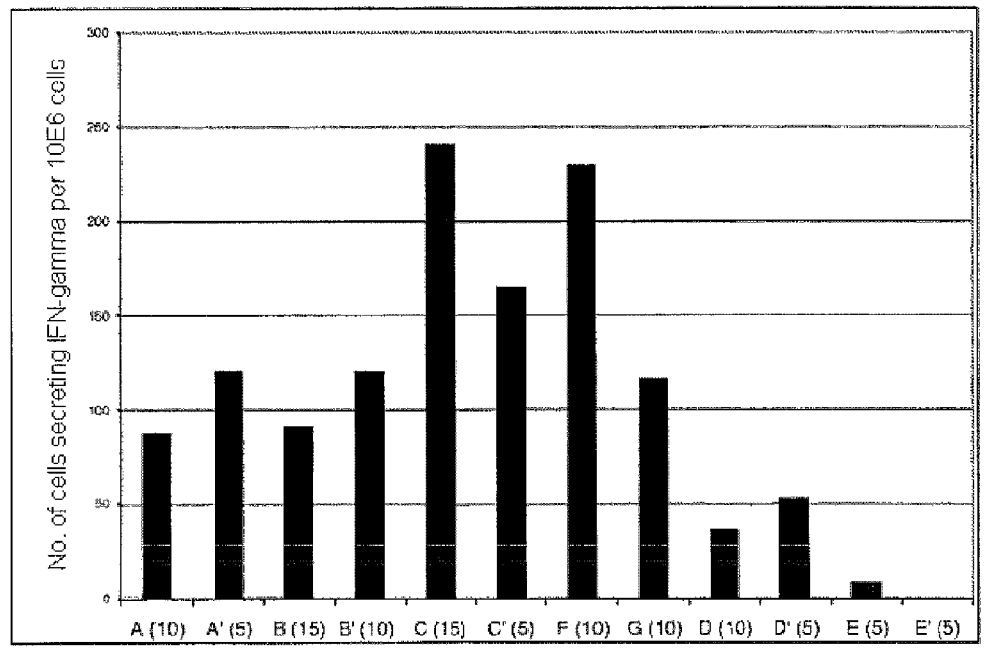
FIG. 3 shows the specific ELISPOT IFN-γ responses of the protein p24 during the 3 immunisation experiments with different vaccine compositions including the compositions according to the invention which comprise the synthetic vector PLA/p24 and the viral vector MVA Gag.

FIG. 3 shows the specific ELISPOT IFN-γ responses of the protein p24. All the animals immunised during the 3 successive experiments were included in the analysis. For each vaccine composition the number of animals which received this composition is indicated in brackets. The Y axis shows the mean number of cells secreting IFN-γ in a specific manner in response to a stimulation for 42 hours by the protein p24 on a million stimulated cells. This response was determined individually for each mouse. The number presented on this graph corresponds to the calculated mean from all the mice of a group (n=5, 10 or 15 depending upon the groups).

Again it is possible to classify the vaccine compositions into several categories as a function of the ELISPOT IFN-γ responses obtained. The best responses are induced by the compositions PLA+MVA (C and C') and DNA+PLA (F). The third injection further decreases the response observed in the case of the composition PLA+MVA (C'). The compositions MVA+PLA (B and B') and MVA+MVA (A and A') enable intermediate intensity responses to be generated, whilst the strategy using only PLA (D and D') only induces low responses Thus we have been able to show that the vaccine composition PLA+MVA was the best choice for inducing a secretion of specific IFN-γ of the protein p24.

5.4 the ELISPOT IL-4 Response Against the Protein p24

Figure 4:
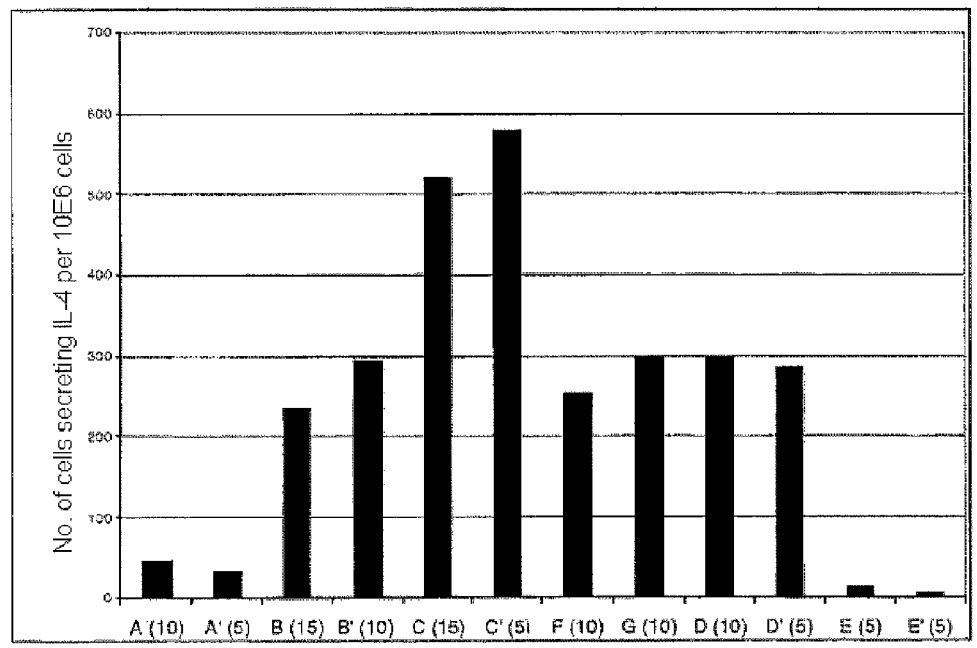
FIG. 4 shows the specific ELISPOT IL-4 responses of the protein p24 during the 3 immunisation experiments with different vaccine compositions including the compositions according to the invention which comprise the synthetic vector PLA/p24 and the viral vector MVA Gag.

FIG. 4 shows the specific ELISPOT IL-4 responses of the protein p24. All the animals immunised during the 3 successive experiments were included in the analysis. For each vaccine composition the number of animals which received this composition is indicated in brackets. The Y axis shows the mean number of cells secreting IL-4 in a specific manner in response to a stimulation for 42 hours by the protein p24 on a million stimulated cells. This response was determined individually for each mouse. The number presented on this graph corresponds to the calculated mean from all the mice of a group (n=5, 10 or 15 depending upon the groups).

Once again it is possible to classify the vaccine compositions into several categories as a function of the ELISPOT IL-4 responses obtained. The best response is induced by the composition PLA+MVA (C and C'). Once again the third injection does not seem necessary since it only slightly improves the response induced by the composition PLA+MVA (C'). The compositions MVA+PLA (B and B') and DNA+PLA (F) and PLA+PLA (D and D') enable intermediate intensity responses to be generated, whilst the strategy using only MVA only induces low responses (A and A').

Thus we have been able to show that the vaccine composition PLA+MVA was the best choice for inducing a secretion of specific IL-4 of the protein p24.

5.5 Secretion of Cytokines

The study of the secretion of cytokines makes it possible to create a table of the state of immune activation of the animal which received the vaccine composition. The cytokines can be divided into four groups as a function of their properties:
1) The mediators of natural immunity (IFN-γ, IL-1, IL-6, IL-8 . . . )
2) The activators of the lymphocyte activation, growth and differentiation (IL-2, IL-4, IL-5, IL-6, IL-10, TGF-β)
3) The non-specific activators of inflammation (IFN-γ, IL-5, IL-8)
4) Activators and differentiators of immature leucocytes (IL-3, GM-CSF)

By the use of a multiplex kit we have been able to dose the secretion of 10 different cytokines in the culture supernatants of the splenocytes obtained from the sacrificed animals. These cytokines are: IFN-γ, TNF-α, GM-CSF, IL-4, IL-17, IL-1α, IL-2, IL-5, IL-6, IL-10.

None of the vaccine compositions tested induces a significant secretion of the cytokines IL-1α and IL-17.

For all the other cytokines tested we have been able to demonstrate the differences between the groups.

Figure 5:
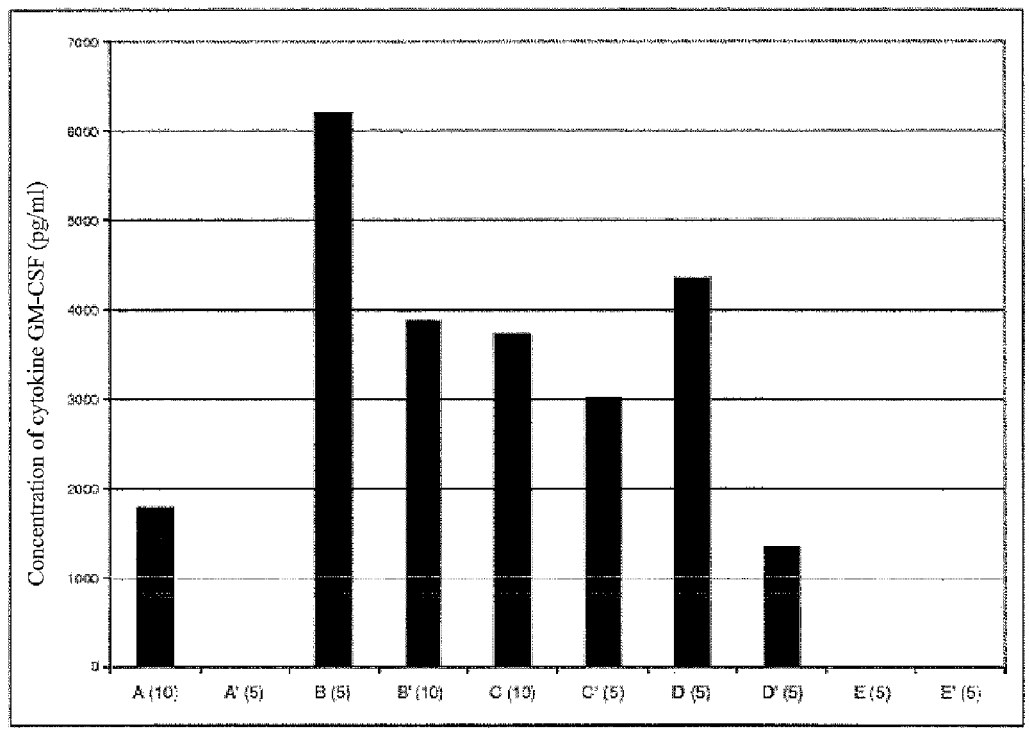
FIG. 5 shows the secretion of the specific cytokine GM-CSF of the protein p24 during the 3 immunisation experiments with different vaccine compositions including the compositions according to the invention which comprise the synthetic vector PLA/p24 and the viral vector MVA Gag.

FIG. 5 shows the secretion of the specific cytokine GM-CSF of the protein p24. All the animals immunised during the 3 successive experiments were included in the analysis when the quantity of cells available permitted it. For each vaccine composition the number of animals which received this composition is indicated in brackets. The cells obtained from mice of one and the same group were pooled before being cultured for the secretion test. The Y axis shows the concentration of GM-CSF (in pg/ml) secreted in the culture medium in response to a stimulation for 3 days by the protein p24.

The cytokine GM-CSF (granulocyte-macrophage colony stimulating factor) is a powerful immunostimulator which enables activation of the immune functions such as adhesion, phagocytosis, etc. of macrophages, neutrophiles and eosinophiles. As we can see in FIG. 5, we have shown a substantial secretion of GN-CSF in the groups containing PLA in association or not with MVA (except for when the number of injections is increased to 3 for the PLAs) whilst the groups immunised exclusively with MVA secretes little or none of it.

Figure 6:
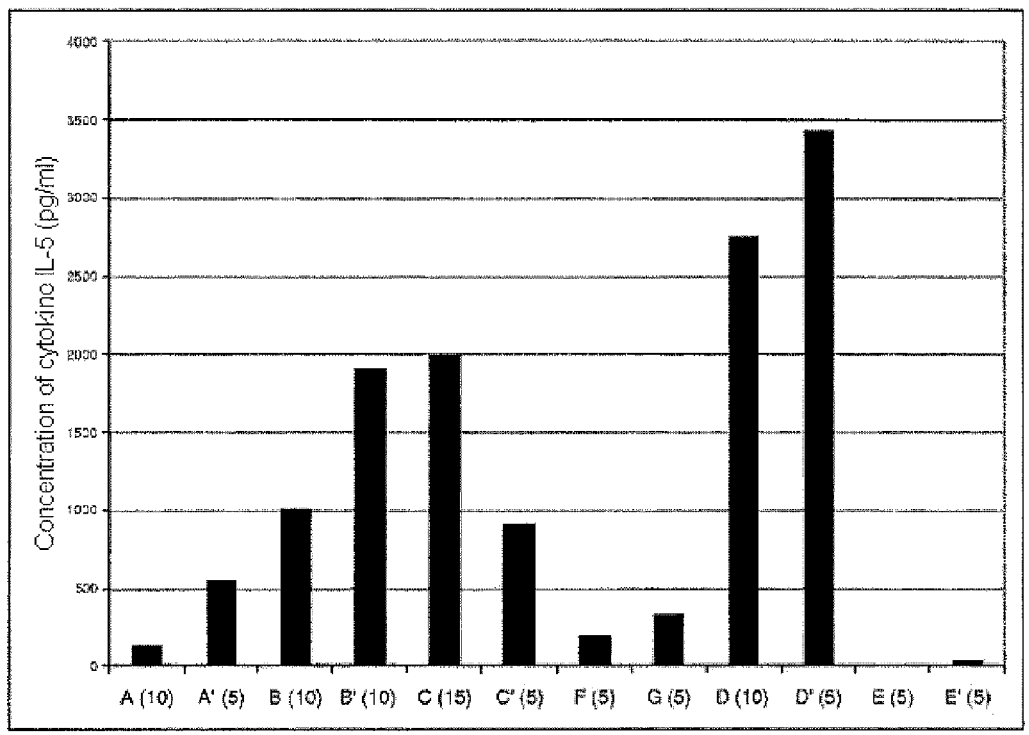
FIG. 6 shows the secretion of the specific cytokine IL-5 of the protein p24 during the 3 immunisation experiments with different vaccine compositions including the compositions according to the invention which comprise the synthetic vector PLA/p24 and the viral vector MVA Gag.

FIG. 6 shows the secretion of the cytokine IL-5 specific of the protein p24. All the animals immunised during the 3 successive experiments were included in the analysis when the quantity of cells available permitted it. For each vaccine composition the number of animals which received this composition is indicated in brackets. The cells obtained from mice of one and the same group were pooled before being cultured for the secretion test. The Y axis shows the concentration of IL-5 (in pg/ml) secreted in the culture medium in response to a stimulation for 3 days by the protein p 24.

For all the type Th2 cytokines tested such as IL-4, IL-5, IL-6 and IL-10 the secretion profiles are very similar to that shown in FIG. 6 which corresponds to the secretion of IL-5. No secretion is observed in the groups which received wild MVA (this is normal, it is a negative control). Low concentrations are obtained for the MVA Gag groups, 2 or 3 injections, and the groups combining DNA and PLA. Average concentrations are obtained for the groups of mice immunised by the compositions PLA and MVA. The strongest concentrations are obtained in the groups which received only PLA. The secretion of cytokines is therefore oriented more or less towards the type Th2 cytokines as a function of the vaccine composition:

- a response mainly of type Th2 is observed for the groups immunised only with PLAs (the secretion of IFN-γ of IL-2, type Th1 cytokines is low (FIG. 7)),
- a non-polarised response both Th1 and Th2 for the groups immunised with the combinations PLA and MVA,
- for the MVA groups the secretion of type Th2 cytokines is low.

We also note that the 4 dosed Th2 cytokines are not secreted at the same concentration. IL-4 and IL-10 are secreted at high levels. The following table recapitulates the mean concentrations of the different cytokines observed in the groups which have received the compositions PLA and MVA.

TABLE 5

| Cytokine | IL-4 | IL-5 | IL-6 | IL-10 |
|---|---|---|---|---|
| Mean conc. (pg/ml) | 2600 | 1460 | 260 | 2660 |

The interleukin 4, IL-4, is secreted by type CD4+T lymphocytes. It increases the growth and the differentiation of the previously activated B lymphocytes, favours the production of IgE which plays an important part in the immediate hypersensitivity reactions. It also activates the macrophages.

The interleukin 5, IL-5, stimulates the growth, the differentiation and the activation of eosinophils which play an important part in the fight against parasitic infections. The increase in the number of eosinophils is not only a sign of parasite attack but also a means of defence. The IL-5 induces the proliferation of B lymphocytes and their secretion of immunoglobulins. It activates cytotoxic T lymphocytes. Its use in the treatment of certain parasitic diseases can be envisaged.

The interleukin 6, IL-6, stimulates the growth and the differentiation of B lymphocytes and increases the generation of platelets. By activation of the hepatocytes it causes the secretion of proteins of inflammation like fibrinogen and reactive protein C. It has a pro-inflammatory role, It has a cytotoxic effect with respect to certain tumours.

Figure 7:
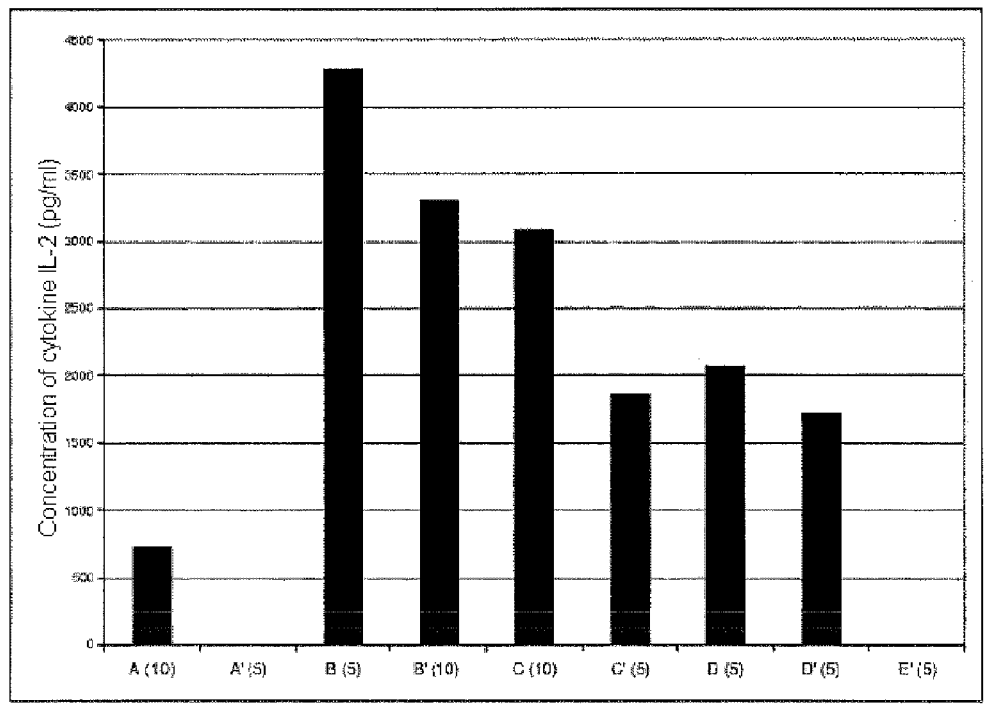
FIG. 7 shows the secretion of the specific cytokine IL-2 of the protein p24 during the 3 immunisation experiments with different vaccine compositions including the compositions according to the invention which comprise the synthetic vector PLA/p24 and the viral vector MVA Gag.

FIG. 7 shows the secretion of the specific cytokine IL-2 of the protein p24. All the animals immunised during the 3 successive experiments were included in the analysis when the quantity of cells available permitted it. For each vaccine composition the number of animals which received this composition is indicated in brackets. The cells obtained from mice of one and the same group were pooled before being cultured for the secretion test. The Y axis shows the concentration of IL-2 (in pg/ml) secreted in the culture medium in response to a stimulation for 3 days by the protein p 24.

IL-2 is a growth factor for T lymphocytes. It activates the transformation thereof into type CD8+ cytotoxic T lymphocytes which secrete interferon α, which stimulates macrophages to release TNFα and TGFα (transforming growth factor α). IL-2 stimulates the growth and the cytolytic activity of NK (natural killer) cells. It stimulates the maturation of B lymphocytes and the synthesis of antibodies. This is a Th1 type cytokine.

It is possible to classify the vaccine compositions into several categories as a function of the secretion of specific IL-2 of the protein p24. The best response is induced by the combination MVA+PLA (B), then PLA+MVA (C), PLA alone (D) and MVA alone (A).

5.6 the Specific Humoral Response of the Protein p24

Figure 8:
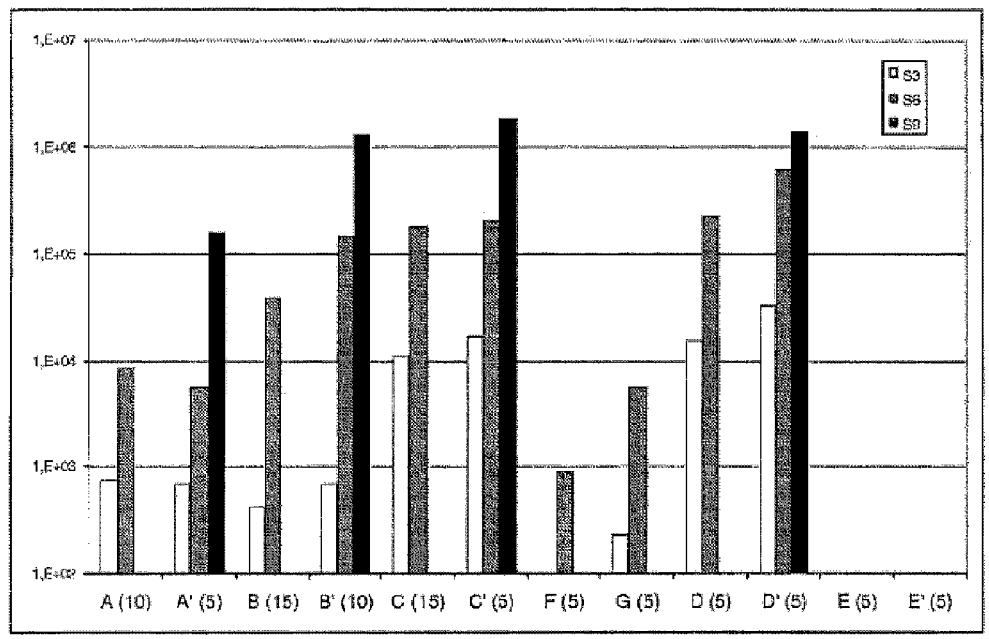
FIG. 8 shows the appearance kinetics of the specific humoral responses of the protein p24 during the 3 immunisation experiments with different vaccine compositions including the compositions according to the invention which comprise the synthetic vector PLA/p24 and the viral vector MVA Gag.

FIG. 8 shows an appearance kinetics of the specific humoral responses of the protein p24. All the animals immunised during the 3 successive experiments were included in the analysis. For each vaccine composition the number of animals which received this composition is indicated in brackets. The Y axis shows the titre of anti-p24 IgG measured by ELISA for capture of p24; the scale of this axis is logarithmic. The titre of antibodies was determined individually for each mouse. The number presented on this graph corresponds to the geometric mean calculated from all the mice of a group (n=5, 10 or 15 depending upon the groups). S3=week 3, S6=week 6, S9=week 9.

In so far as the anti-p24 humoral responses are concerned, for the first time in this series of experiments increasing the number of injections makes it possible to significantly improve the measured immune response. For, regardless of the group studied, changing from 2 to 3 injections of immunogen increases the anti-p24 response by approximately 1 log (except for the group of PLA alone where the increase is lower but nevertheless significant).

For the groups which received 3 injections, all the combinations containing MVA and PLA or PLA alone induce a high titre ($10^E6$) higher by one log than the titre induced by MVA alone.

In a similar manner, for the groups which received 2 injections, all the compositions containing MVA and PLA or PLA alone induce a high titre, higher by one log than the titre induced by MVA alone.

Changing an injection of PLA to MVA in a vaccination scheme does not harm the antibody titres but makes it possible to widen the cell responses with respect to those which are generated solely by a PLA vector.

Conclusion:

As a function of the type of response analysed, the best composition is not always the same, as certain compositions specifically obtain very good responses.

However, in order to obtain a wide and intense immune response, the best composition is the composition PLA+MVA.

EXAMPLE 2

Immunisation of Mice with the Vaccine Composition PLA/p24 Microparticles and Adenovirus Gag 1. Animal Model The immunisation experiments were carried out in female BALB/c ($H-2K^d$) mice aged from 6 to 8 weeks at the time of the first immunisation.

2. Immunogens Administered

In this series of experiments the following immunogens were used alone or in combination:
- microparticles PLA/p24 prepared according the solvent displacement procedure of Patent Application WO2005/027871.
- Adenovirus type 5 Gag which is recombinant for the Gag gene of the HIV-1 virus, coding for the protein p24. (Généthon)
- Adenovirus type 5 eGFP which is recombinant for the enhanced Green Fluorescent Protein (Généthon). It is a negative control which serves to measure whether the viral vector induces a non-specific immune response during the immunisations.
- DNA Gag. The Gag gene (SEQ ID No. 1) was cloned in the eukarytic expression plasmid phCMV (non-commercial plasmid). DNA preparations without endotoxins and in large quantity have been produced with the Gigaprep endotoxin-free kit from Macherey-Nagel. The DNA serves as positive control, since it is known that in mice the administration of naked DNA by the intramuscular route makes it possible to induce a good cytotoxic response (CTL).

3. Immunisations 30 mice received 2 doses of the immunogens described in point 2 above at 0 to 3 weeks. The vaccine compositions received by each group of mice are indicated in Table 6 below. All the injections were carried out by the intramuscular route for the adenovirus and the DNA and subcutaneously for the PLAs.

TABLE 6

| Dose 1st injection Week 0 | Dose 2nd injection Week 3 | Number of mice | Composition |
|---|---|---|---|
| Ad5 Gag $10^8$ ip | Ad5 Gag $10^8$ ip | 5 | H |
| Ad5 Gag $10^8$ ip | PLA/p24 40 µg | 5 | I |
| PLA/p24 40 µg | Ad5 Gag $10^8$ ip | 5 | J |
| Ad5 Gag $10^7$ ip | Ad5 Gag $10^7$ ip | 5 | H' |
| Ad5 Gag $10^7$ ip | PLA/p24 40 µg | 5 | I' |
| PLA/p24 40 µg | Ad5 Gag $10^7$ ip | 5 | J' |

The animals were sacrificed 3 weeks after the last injection and the blood and the spleen were removed for immunological analyses.

4. Immunological Analyses

Carried out to the same procedures as in Example 1. Moreover, we have measured the humoral responses directed against the adenovirus5 using an ELISA technique. The procedure is identical to that used for the anti-p24 ELISA, except that an adenovirus lysate is used in capture.

5. Results 5.2 CTL Responses

Figure 9:
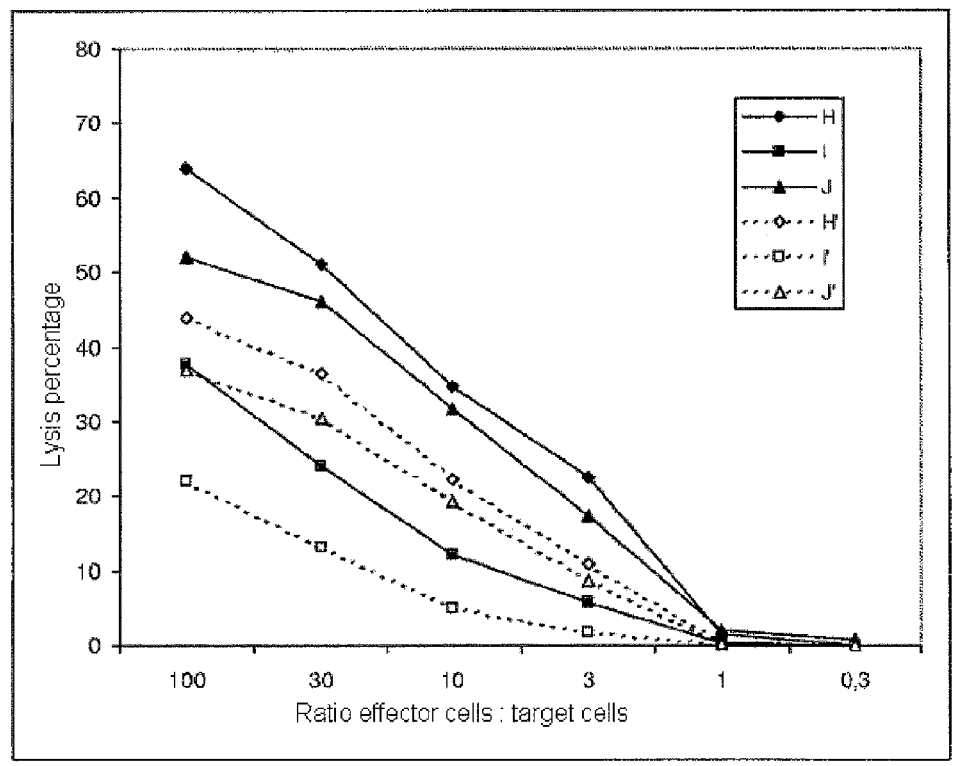
FIG. 9 shows the CTL responses during the immunisation experiment No. 2 with different vaccine compositions including the compositions according to the invention which comprise the synthetic vector PLA/p24 and the viral vector Adenovirus Gag.

FIG. 9 shows the CTL responses obtained during the immunisation experiment No. 2. Each group consist of 5 mice, analysed individually. As the non-specific stimulation (without peptide) in all the groups is 0 it is not shown. The X axis corresponds to the ratio of effector cells (CTL) to target cells (to be lysed). The Y axis corresponds to the mean lysis percentage; this is the arithmetic mean calculated from all the mice of a group (n=5).

In all the groups 5 mice out of 5 developed a CTL response, except for one mouse of the Ad5Gag $10^7$+PLA group.

The same thing is observed for the 2 doses of virus tested: the combinations Ad+Ad (H and H') and PLA Ad (J and J') induce better CTL responses than the combination Ad+PLA (I and I').

5.3 the ELISPOT IFN-γ Response Against the Gag Peptide AMQ

Figure 10:
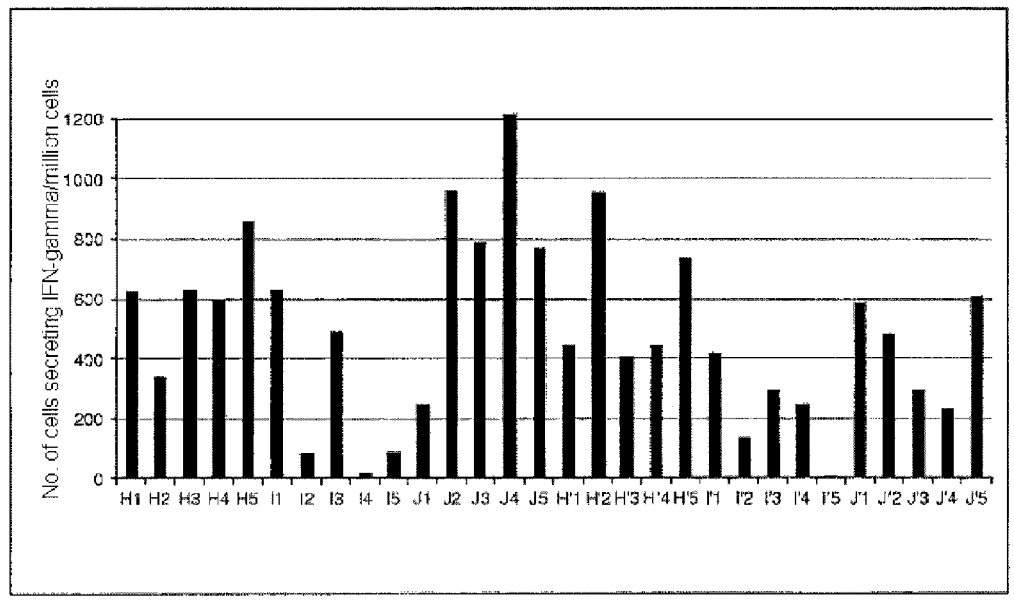
FIG. 10 shows the specific ELISPOT IFN-γ responses of the Gag AMQ peptide after immunisation with different vaccine compositions including the compositions according to the invention which comprise the synthetic vector PLA/p24 and the viral vector Adenovirus Gag.

FIG. 10 shows the specific ELISPOT IFN-γ responses of the Gag peptide AMQ. The Y axis shows the mean number of cells secreting the IFN-γ in a specific manner in response to a stimulation for 18 hours by the Gag peptide AMQ on one million stimulated cells. This response was determined individually for each mouse (numbered from 1 to 5 for each mouse, thus H1 corresponds to the mouse 1 which had received the composition H Ad5 Gag $10^8$ ip and Ad5 Gag $10^8$ ip, etc. The number presented on this graph corresponds to a mean of triplicates.

It may be noted from FIG. 10 that:
- at $10^8$: the response PLA+Ad>Ad+Ad>Ad+PLA
- at $10^7$: the response Ad+Ad≥PLA+Ad>Ad+PLA. The difference between the compositions Ad+Ad and PLA+Ad is not very clear. Overall the ELISPOT IFN-γ response is in concordance with the CTL test: The compositions PLA+Ad and Ad+Ad are more effective than Ad+PLA.

5.4 Secretion of Cytokines

As in Example 1, we tested the secretion of 10 cytokines in the supernatant. Amongst these IL-5, IL-6, IL-17 and IFN-γ were not secreted or were secreted at infinitesimal concentrations. As for GM-CSF, TNF-α and IL-1α, their secretion was not specific for the protein p24 by the dosage technique used. It is very probable that it is the immunisation by the adenovirus which causes the secretion of these cytokines. If a specific secretion of the protein p24 exists, it is embedded in that caused by the adenovirus.

For 3 other cytokines, namely IL-2 (Th1), as well as IL-4 and IL-10 (Th2), we were able to measure the specific secretion of the protein p24. The results are presented in FIG. 11.

Figure 11:
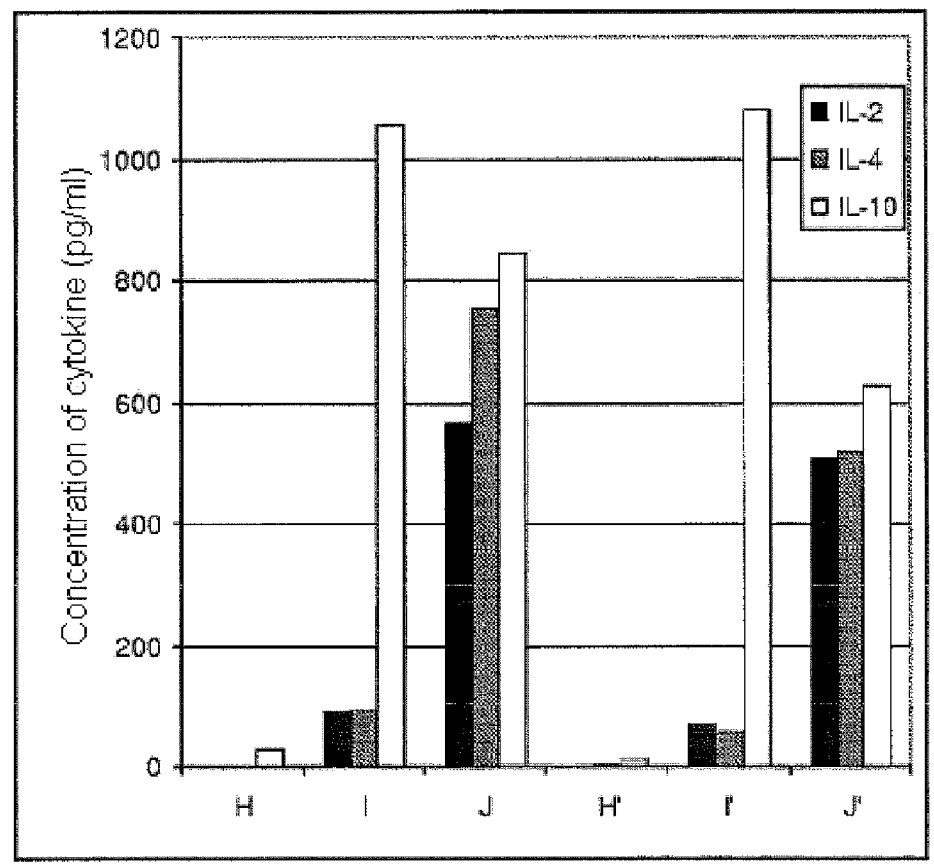
FIG. 11 shows the specific secretion of the protein p24 of the cytokines IL-2, IL-4, IL-10 after immunisation with different vaccine compositions including the compositions according to the invention which comprise the synthetic vector PLA/p24 and the viral vector Adenovirus Gag.

FIG. 11 shows the secretion of the cytokines IL-2, IL-4 and IL-10 specific for the protein p24. Each vaccine composition was administered to 5 mice. The cells obtained from mice of one and the same group were pooled before being cultured for the secretion test. The Y axis shows the concentration of each cytokine (in pg/ml) secreted in the culture medium in response to stimulation for 3 days by the protein p24.

The results in FIG. 11 show that:
- the composition Ad5 Gag+Ad5 Gag (H and H') does not give any secretion of IL-2, IL-4 or IL-10.
- only the composition PLA+Ad5 Gag (J and J') gives a secretion of IL-2 and IL-4.
- the compositions PLA+Ad5 Gag (J and J') and Ad5 Gag+PLA (I and I') enable a secretion of IL-10.

The composition Ad+Ad (H and H') induces a rather polarised Th1 cytokine response (measured by ELISPOT IFN-γ).

The composition PLA+Ad 5 (J and J') induces a non-polarised cytokine response, since not only Th1 cytokines such as IFN-γ (by ELISPOT) and IL-2, but also Th2 cytokines such as IL-4 and IL-10 are detected.

5.5 Humoral Responses

Figure 12:
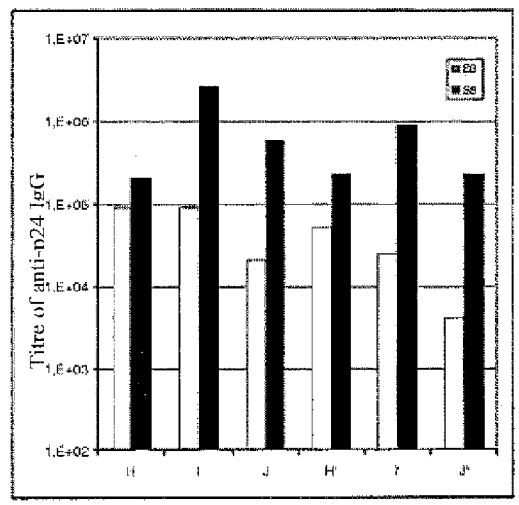
FIG. 12 shows the appearance kinetics of the specific humoral responses of the protein p24 (12A) or of the adenovirus (12B) after immunisation with different vaccine compositions including the compositions according to the invention which comprise the synthetic vector PLA/p24 and the viral vector Adenovirus Gag.
Figure 12:
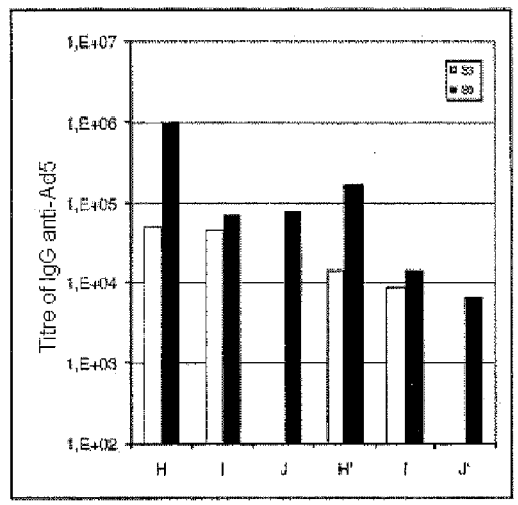

FIG. 12 shows the appearance kinetics of the humoral responses. FIG. 12(A) shows the antibody response directed against the protein p24 and FIG. 12(B) shows the antibody response directed against the adenovirus. Each vaccine composition was administered to 5 mice. The Y axis shows the titre of IgG measured by ELISA; the scale of this axis is logarithmic. The titre of antibodies was determined individually for each mouse. The number presented on this graph corresponds to the geometric mean calculated from all the mice of a group (n=5). S3=week 3, S6=week 6.

The anti-adenovirus response (or anti-vector response) is approximately 1 log less in the groups which received the compositions Ad+PLA (I and I') and PLA+Ad (J and J') than for Ad+Ad (H and H').

The compositions according to the invention therefore make it possible to decrease the anti-adenovirus immunity.

EXAMPLE 3

Comparison of the Vaccine Compositions PLA/p24+MVA Gag and Alum/p24+MVA Gag in Mice 1. Animal Model The immunisation experiments were carried out in female BALB/c (H-2K$^d$) mice aged from 6 to 8 weeks at the time of the first immunisation.

2. Immunogens administered

In this series of experiments the following immunogens were used alone or in combination:
- microparticles PLA/p24 prepared according the solvent displacement procedure of Patent Application WO2005/027871.
- alum/p24: the alum (Imject Alum, Pierce, catalogue No. 77161) is mixed volume for volume (1:1) with the protein p24 diluted in PBS. A dose of 40 µg of p24 is administered per injection and per animal.
- the MVA Gag virus (Modified Vaccinia Virus Ankara, attenuated vaccinia virus, Ankara strain) which is recombinant for the Gag gene of the HIV-1 virus, coding for the protein p24. The recombinant virus was constructed at Transgene, as indicated in Example 1.
- DNA Gag. The Gag gene (SEQ ID No. 1) was cloned in the eukarytic expression plasmid phCMV. DNA preparations without endotoxins and in large quantity have been produced with the Gigaprep endotoxin-free kit from Macherey-Nagel. The DNA serves as positive control, since it is known that in mice the administration of naked DNA by the intramuscular route makes it possible to induce a good cytotoxic response (CTL).

3. Immunisations 30 mice received 2 doses of the immunogens described in point 2 above at 0 and 3 weeks. The vaccine compositions received by each group of mice are indicated in Table 7 below. All the injections were carried out subcutaneously except for the DNA which was administered by the intramuscular route.

TABLE 7

| Dose 1st injection Week 0 | Dose 2nd injection Week 3 | Number of mice | Composition |
|---|---|---|---|
| MVA Gag 10$^7$ pfu | PLA/p24 40 µg | 5 | B |
| PLA/p24 40 µg | MVA Gag 10$^7$ pfu | 5 | C |
| MVA Gag 10$^7$ pfu | Alum/p24 40 µg | 5 | K |
| Alum/p24 40 µg | MVA Gag 10$^7$ pfu | 5 | L |
| PLA/p24 40 µg | DNA Gag 5 µg (IM) | 5 | G |
| Alum/p24 40 µg | DNA Gag 5 µg (IM) | 5 | M | pfu = plaque forming units, this is the unit of measurement of the dose of MVA used. The viral titre is expressed in pfu according to the technique of dosage of the viral stock used.

The animals were sacrificed 6 weeks after the first injection and the blood and the spleen were removed for immunological analyses.

4. Immunological Analyses

Carried out according to the same procedures as in Example 1. Moreover, we have measured the humoral responses directed against the MVA using an ELISA technique. The procedure is identical to that used for the anti-p24 ELISA, except that a MVA lysate is used in capture.

5. Results 5.1 the ELISPOT IFN-γ Response Against the Gag Peptide AMQ

FIG. 13 shows the specific ELISPOT IFN-γ responses of the Gag peptide AMQ. The Y axis shows the mean number of cells secreting the IFN-γ in a specific manner in response to a stimulation for 18 hours by the Gag peptide AMQ on one million stimulated cells. This response was determined individually for each mouse. The number presented on this graph corresponds to the mean calculated from all the mice in a group (n=5).

The ELISPOT IFN-γ responses obtained during this experiment are lower than usual. This drop is observed both for the tested groups and the control groups, and it is linked to the progress of the experiment. For this reason, as we seek to compare the different combinations with one another, this experiment remains interpretable and shows clearly that the composition PLA/p24+MVA Gag (C) induces a better secretion of IFN-γ measured by ELISPOT than the other groups tested, namely MVA Gag+PLA/p24 (B), MVA Gag+alum/p24 (K), alum/p24+MVA Gag (L).

5.2 the ELISPOT IL-4 Response Against the Protein p24

FIG. 14 shows the specific ELISPOT IL-4 responses of the protein p24. The Y axis shows the mean number of cells secreting IFN-γ in a specific manner in response to a stimulation for 42 hours by the protein p24 on a million stimulated cells. This response was determined individually for each mouse. The number presented on this graph corresponds to the calculated mean from all the mice of a group (n=5).

For the induction of a type IL-4 ELISPOT response, the best immunogen consists of the combination MVA Gag and PLA/p24 (B and C). Regardless of the order of administration of this composition, the IL-4 responses obtained are greater than those induced by the compositions MVA Gag+alum/p24 (regardless of the order) (K and L), PLA/p24+DNA Gag (G) and alum/p24+DNA Gag (M). If the order of administration of the products is now considered, it is always the composition PLA/p24+MVA Gag (C) which gives better results than the inverse combination MVA Gag+PLA/p24 (B).

5.3 the Specific Humoral Response of the Protein p24

FIG. 15 shows an appearance kinetics of the specific humoral responses of the protein p24. The Y axis shows the titre of anti-p24 IgG measured by p24 capture ELISA; the scale of this axis is logarithmic. The titre of antibodies was determined individually for each mouse. The number presented on this graph corresponds to the geometric mean calculated from all the mice of a group (n=5), S2=week 2, S4=week 4, S6=week 6.

For the induction of a specific protein p24 antibody response, the best immunogen again consists of the combination MVA Gag and PLA/p24 (B and C). Regardless of the order of administration of this composition, the titres of anti-P4 IgG obtained are 0.6 to 1.2 log higher at week 6 than those induced by the compositions MVA Gag+alum/p24 (regardless of the order) (K and L), PLA/p24+DNA Gag (G) and alum/p24+DNA Gag (M). If the order of administration of the products is now considered, it is always the composition PLA/p24+MVA Gag (C) which gives better results than the inverse combination MVA Gag+PLA/p24 (B), but only by 0.4 log.

5.4 the Specific Humoral Response of the MVA Virus

FIG. 16 shows the appearance kinetics of the specific humoral responses of the MVA virus. The Y axis shows the titre of anti-MVA IgG measured by ELISA for capture of MVA. The titre of antibodies was determined individually for each mouse. The number presented on this graph corresponds to the geometric mean calculated from all the mice of a group (n=5). S4=week 4, S6=week 6.

In the groups PLA/p24+MVA Gag (C) and alum/p24+MVA Gag (L), the MVA was administered at week 3. As we can see in FIG. 16, the anti-MVA response did not have time to become established at the time of the analysis, at week 6. On the other hand, in the groups which received the MVA injection first it is possible to measure the anti-vector response. Surprisingly, from 4 weeks the anti-MVA response is much lower in the group MVA Gag+PLA/p24 (B) than in the group MVA Gag+alum/p24 (K). Moreover, with the combination MVA Gag+PLA/p24 the anti-MVA titre does not increase in time, which is not the case with the combination MVA Gag+alum/p24.

In association with MVA the PLAs make it possible to limit the anti-MVA antibody response although this is not the case with the combination MVA+alum. This is a very interesting and very useful property for immunisation and vaccination applications.

Conclusion:

The compositions according to the invention PLA/p24 and MVA Gag make it possible to induce better cell and humoral responses than the compositions alum/p24 and MVA Gag. Moreover, they make it possible to limit the anti-vector response.

EXAMPLE 4

Intranasal Administration of the Vaccine Compositions PLA/p24 and MVA Gag

1. Animal Model

The immunisation experiments were carried out in female BALB/c (H-2K$^d$) mice aged from 6 to 8 weeks at the time of the first immunisation.

2. Immunogens Administered

In this series of experiments the following immunogens were used alone or in combination:
  microparticles PLA/p24 prepared according the solvent displacement procedure of Patent Application WO2005/027871.
  the MVA Gag virus (Modified Vaccinia Virus Ankara, attenuated vaccinia virus, Ankara strain) which is recombinant for the Gag gene of the HIV-1 virus, coding for the protein p24. The recombinant virus was constructed at Transgene, as indicated previously.

3. Immunisations 10 mice received 3 doses of the immunogens described in point 2 above at 0, 10 and 20 days. The vaccine compositions received by each group of mice are indicated in Table 8 below. All the injections were carried out intranasally.

TABLE 8

| Dose 1st injection Day 0 | Dose 2nd injection Day 10 | Dose 3rd injection Day 20 | Number of mice |
|---|---|---|---|
| PLA/p24 20 µg | PLA/p24 20 µg | MVA Gag $10^7$ pfu | 5 |
| MVA Gag $10^7$ pfu | MVA Gag $10^7$ pfu | PLA/p24 20 µg | 5 | pfu = plaque forming units, this is the unit of measurement of the dose of MVA used. The viral titre is expressed in pfu according to the technique of dosage of the viral stock used.

The animals were sacrificed 32 days after the first injection. The blood, vaginal secretions, faeces, spleen and genital apparatus (vagina) were removed for immunological analyses.

4. Immunological Analyses

Carried out according to the same procedures as in Example 1.

5. Results

Recapitulation of the experimental data

TABLE 9

| Vaccine combinations | PLA/p24, PLA/p24, MVA Gag | MVA Gag, MVA Gag, PLA/p24 |
|---|---|---|
| Number of mice which developed a CTL response | 2/5 | 2/5 |
| % lysis means of mice CTL+ | 50% | 45% |

The ELISPOT measures the number of cells secreting cytokine per $10^E6$ cells analysed

| | | |
|---|---|---|
| ELISPOT IFN-γ, AMQ, blood | 155 | 79 |
| ELISPOT IFN-γ, p24, blood | 146 | 94 |
| ELISPOT IL-4, AMQ, blood | 50 | 10 |
| ELISPOT IL-4, p24, blood | 126 | 32 |
| ELISPOT IFN-γ, AMQ, vaginal | 1550 | 754 |
| ELISPOT IL-4, AMQ, vaginal | 0 | 0 |
| ELISPOT IL-4, p24, vaginal | 0 | 0 |
| Titre of anti-p24 IgG of the serum (determined by ELISA) | 68 000 | 200 000 |
| Titre of anti-p24 IgA of the vaginal secretions (determined by ELISA) | 18 | 8 |
| Titre of anti-p24 IgG of the vaginal secretions (determined by ELISA) | 124 | 616 |
| Anti-p24 IgA in the faeces (absorbency at 450 nm, determined by ELISA) | J 20   0.20<br>J 32   0.02 | J20   0.18<br>J32   0.03 |

-continued

| | | | | |
|---|---|---|---|---|
| Anti-p24 IgG in the faeces (absorbency at 450 nm, determined by ELISA) | J 20 J 32 | 0.17 0.69 | J20 J32 | 0.17 0.60 |

The intranasal administration of the combinations PLA/p24 and MVA Gag makes it possible to induce both a measured systemic immune response in the taking of blood and spleen, and a peripheral immune response at the mucous level, in particular at the level of the urogenital tract. Each time, the two arms of the immune system are activated: at the level of these two sites it has been possible to demonstrate cell and humoral immune responses directed against the protein p24. The capacity to induce a wide peripheral response at the level of the urogenital tract constitutes a considerable advantage for the combinations PLA/p24 and MVA Gag in the vaccine applications for prophylactic or therapeutic purposes.

EXAMPLE 5

Immunisation of Mice with the Vaccine Combination of PLA/Beta-Gal Microparticles and MVA Beta-Gal Virus 1. Animal Model The immunisation experiments were carried out in female BALB/c (H-2K$^d$) mice aged from 6 to 8 weeks at the time of the first immunisation.

2. Immunogens Administered

In this series of experiments the following immunogens were used alone or in combination:
  microparticles PLA/beta-gal prepared according the solvent displacement procedure of Patent Application WO2005/027871.
  the MVA beta-gal virus (modified vaccinia virus Ankara, attenuated vaccinia virus, Ankara strain) which is recombinant for the lacZ gene of *E. coli*, coding for the enzyme beta-galactosidase (beta-gal). The recombinant virus was constructed at Transgene, and produced and purified as described previously.

3. Immunisations 35 mice received 2 doses of the immunogens described in point 2 above at 0 to 3 weeks. The vaccine compositions received by each group of mice are indicated in Table 10 below. All the injections were carried out subcutaneously.

TABLE 10

| Code | Dose 1st injection Week 0 | Dose 2nd injection Week 3 | Number of mice |
|---|---|---|---|
| M | PLA/beta-gal 40 µg | PLA/beta-gal 40 µg | 5 |
| N | MVA beta-gal 10$^7$ pfu | MVA beta-gal 10$^7$ pfu | 5 |
| O | PLA/beta-gal 40 µg | MVA beta-gal 10$^7$ pfu | 5 |
| P | MVA beta-gal 10$^7$ pfu | PLA/beta-gal 40 µg | 5 |
| Q | PLA/beta-gal 40 µg + MVA beta-gal 10$^7$ pfu | | 5 |
| R | | PLA/beta-gal 40 µg + MVA beta-gal 10$^7$ pfu | 5 |
| S | PLA/beta-gal 40 µg + MVA beta-gal 10$^7$ pfu | PLA/beta-gal 40 µg + MVA beta-gal 10$^7$ pfu | 5 | pfu = plaque forming units, this is the unit of measurement of the dose of MVA used. The viral titre is expressed in pfu according to the technique of dosage of the viral stock used.

The animals were sacrificed 6 weeks after the first injection and the blood and the spleen were removed for immunological analyses.

4. Immunological Analyses

The humoral response and the cell response were researched as follows:
  Cell response: after sacrifice of the mice, the spleens were removed in a sterile manner in order to prepare a cell suspension. ELISPOT makes it possible to determine the number of cells secreting a given cytokine in response to a specific stimulus. We are interested in the cytokines IFN-γ of type Th1. The cell suspensions obtained from the spleens were restimulated in vitro by the peptide TPH (TPHPARIGL—SEQ ID No. 3) for 20 hours in order to analyse the responses of type CD8. The 96-well ELISPOT plates with PVDF membranes (Multiscreen IP, Millipore) were coated by an anti-IFN-γ antibody. During the restimulation the suspensions of splenocytes were incubated in these plates in such a way as to capture the cytokines secreted by each cell. The spots corresponding to each cell secreting the relevant cytokine were revealed by a specific biotinylated detection antibody of the relevant cytokine.
  Humoral response: blood was taken from the mice before they were sacrificed. The presence of anti-beta-gal antibodies was determined by ELISA. The protein beta-gal was used in capture and the specific antibodies present in the serum were revealed by a polyclonal anti-mouse antibody as detection antibody which is an Affinipure goat anti-mouse IgG antibody conjugated with horseradish peroxidase (H+L, Jackson Immunoresearch, Cat no 115-035-062). The titre is the inverse of the dilution for which an absorbency of 0.1 OD unit is obtained with the ELISA protocol used.

5. Results 5.1 the ELISPOT IFN-γ Response Against the Gag Peptide AMQ

The results are presented in FIG. 17 which shows the specific ELISPOT IFN-γ responses of the beta-gal peptide TPH. The Y axis shows the mean number of cells secreting IFN-γ in a specific manner in response to a stimulation for 18 hours by the beta-gal peptide TPH on one million stimulated cells. This response was determined individually for each mouse. The number presented on this graph corresponds to the mean calculated from all the mice in a group (n=5).

These results demonstrate that it is possible to classify the vaccine combinations into several categories as a function of the ELISPOT IFN-γ responses obtained. The best responses are induced by the combinations PLA+MVA in separate injections (O) or two simultaneous injections (S). Intermediate responses are obtained with one single injection of PLA+MVA at the same time (groups Q and R). The lower responses are observed with the groups only containing one single immunogen PLA alone (M) or MVA alone (N).

Thus also in the beta-galactosidase we have been able to show that the vaccine combination PLA+MVA was better than the combination MVA+MVA for inducing a secretion of specific IFN-γ of the peptide TPH. Moreover, the order of injection also seems to be important because amongst all the combinations PLA+MVA tested it is the group O, PLA then MVA, which made it possible to obtain the best result. It should be noted that it is also the same combination which was shown to be most effective in the p24 model (Example 1).

5.2 the Specific Humoral Response of the Protein Beta-Gal

The results are presented in FIG. 18 which compares the appearance kinetics of the specific humoral responses of the protein beta-gal. The Y axis shows the titre of anti-beta-gal IgG measured by beta-gal capture ELISA; the scale of this axis is logarithmic. The titre of antibodies was determined individually for each mouse. The number presented on this graph corresponds to the mean calculated from all the mice of a group (n=5). S3=week 2, S6=week 6.

These results show that the best humoral responses are obtained for the group PLA+PLA (M). The titres induced in mice which received PLA and MVA at each injection (S) are comparable. In the groups O, P, Q and R the titres are lower by approximately one log. Amongst all the combinations tested, the poorest inducer of anti-beta-gal antibodies is MVA+MVA. In the beta-galactosidase model, as in the p24 model, all the combinations containing MVA and PLA induce a high titre, higher by one log than the titre induced by MVA alone.

As in Example 1 (p24) changing an injection from PLA to MVA in a vaccination scheme does not to much harm to the titres of antibodies obtained but makes it possible to widen the cell responses with respect to those which are generated solely by a PLA vector.

Even if the PLA+MVA (S) immunisation does not make it possible to induce the best immune response according to each type of response analysed, overall it is the group for which the widest and most intense responses are observed.

EXAMPLE 6

Immunisation of Mice with the Vaccine Combination of CPL/p24 Microparticles and MVA Gag Virus 1. Animal Model The immunisation experiments were carried out in female BALB/c (H-2K$^d$) mice aged from 6 to 8 weeks at the time of the first immunisation.

2. Immunogens Administered

In this series of experiments the following immunogens were used alone or in combination:

the CPL microparticles used in this work are formed by coprecipitation of two polysaccharides; chitosan (Mahtani chitosan PVT Batch 124) and dextran sulphate (Sigma: 31404). The two polymers are previously dissolved in water at pH 4 containing 50 mM of NaCl. The solutions are left with magnetic agitation for 12 hours before preparation of the particles. Then 20 ml of the 0.1% chitosan solution (molar mass of 105000 g/mol and a degree of acetylation 9) are mixed with 9.35 ml of the 0.1% dextran sulphate solution. The deficient solution is poured rapidly onto the excess solution which is agitated magnetically at 1000 rpm. The mixture is left for 30 seconds on the agitator at 500 rpm, then it is centrifuged for 30 minutes at 7800 g. The supernatant is eliminated by reversal, the residue is taken up in water then centrifuged again for 30 minutes at 8000 g. The residues thus obtained are taken up in water and kept at ambient temperature with constant agitation. The particles obtained are characterised by a measurement of size (Coulter granulometer) and of charge (Malvern Zetasizer).

For the adsorption of the protein p24 on the CPLs, the p24 at 1 g/l in phosphate buffer 10 mM pH 5.7 is mixed volume for volume with CPL particles with 1% solids, that is to say final 0.5%. The samples are agitated on a wheel at ambient temperature for 20 hours. After incubation the tubes are recovered and centrifuged for 10 minutes at 1800 g at 20° C. The supernatants are recovered and centrifuged for 15 minutes at 3000 g at 20° C. to eliminate the particles which may remain in suspension, then the protein concentration is determined using a BCA dosage (BCA Protein Assay kit, Pierce: 23225). The residues are taken up in 400 µl of 10 mM phosphate buffer. The particles obtained are characterised by a measurement of size and charge.

the MVA Gag virus (Modified Vaccinia Virus Ankara, attenuated vaccinia virus, Ankara strain) which is recombinant for the Gag gene of the HIV-1 virus, coding for the protein p24. The recombinant virus was constructed at Transgene, and produced and purified as described above.

3. Immunisations 35 mice received 2 doses of the immunogens described in point 2 above at 0 to 3 weeks. The vaccine combinations received by each group of mice are indicated in Table 11 below. All the injections were carried out subcutaneously.

TABLE 11

| Code | Dose 1st injection Week 0 | Dose 2nd injection Week 3 | Number of mice |
| --- | --- | --- | --- |
| T | CPL/p24 10 µg | CPL/p24 10 µg | 5 |
| U | MVA Gag $10^7$ pfu | MVA Gag $10^7$ pfu | 5 |
| V | CPL/p24 10 µg | MVA Gag $10^7$ pfu | 5 |
| W | MVA Gag $10^7$ pfu | CPL/p24 10 µg | 5 |
| X | CPL/p24 10 µg + MVA Gag $10^7$ pfu |  | 5 |
| Y |  | CPL/p24 10 µg + MVA Gag $10^7$ pfu | 5 |
| Z | CPL/p24 10 µg + MVA Gag $10^7$ pfu | CPL/p24 10 µg + MVA Gag $10^7$ pfu | 5 | pfu = plaque forming units, this is the unit of measurement of the dose of MVA used. The viral titre is expressed in pfu according to the technique of dosage of the viral stock used.

The animals were sacrificed 6 weeks after the first injection and the blood and the spleen were removed for immunological analyses.

4. Immunological Analyses

Carried out according to the same procedures as in Example 1.

5. Results 5.1 the ELISPOT IFN-γ Response Against the Gag Peptide AMQ

The results are presented in FIG. 19 which shows the specific ELISPOT IFN-γ responses of the p24 peptide AMQ. The Y axis shows the mean number of cells secreting IFN-γ in a specific manner in response to a stimulation for 18 hours by the p24 peptide AMQ on one million stimulated cells. This response was determined individually for each mouse. The number presented on this graph corresponds to the mean calculated from all the mice in a group (n=5).

These results show that it is possible to classify the vaccine combinations into several categories as a function of the ELISPOT IFN-γ responses obtained. The best response is induced by the combination MVA+MVA (U). The second category contains the combinations CPL+MVA in separate injections (V) or two simultaneous injections (Z). One single simultaneous injection of CPL and MVA (X and Y) is not effective enough to induce a high ELISPOT IFN-γ response. Finally, the combination CPL+CPL (T) is the less effective.

As for the combination PLA+MVA, the combination CPL+MVA is effective for inducing a secretion of specific IFN-γ of the peptide AMQ. However, the simultaneous injection of the two immunogens does not make it possible to improve performances with respect to administration separated by 3 weeks (Z vs V).

5.2 the Specific Humoral Response of the Protein p24

The results are presented in FIG. 20 which compares the appearance kinetics of the specific humoral responses of the protein p24. The Y axis shows the titre of anti-p24 IgG measured by ELISA for capture of p24; the scale of this axis is logarithmic. The titre of antibodies was determined individually for each mouse. The number presented on this graph corresponds to the mean calculated from all the mice of a group (n=5). S3=week 2, S6=week 6.

These results show that for the groups which received 2 injections all the combinations containing CPL and MVA (V, W, Z) or CPL alone (T) induce a high titre ($10^E6$), higher by 2-3 log than the titre induced by MVA alone. However, the combination CPL+MVA (V) is more effective than the inverse order of injection (W). In the groups which received only one single injection of CPL and MVA (X and Y), the titres of antibodies are lower, but nevertheless higher than what is obtained with MVA alone.

As for the combination PLA+MVA, changing an injection from CPL to MVA in a vaccination scheme does not harm the titres of antibodies obtained but makes it possible to considerably increase the cell responses with respect to those which are generated solely by a CPL vector.

Conclusions:

All of the examples enable us to show that the combination of a colloidal synthetic bioresorbable vector, such as PLA, CPL, and a viral vector, such as MVA and adenovirus, makes it possible to induce effective and wide immune responses. To be most effective, the combination should preferably be administered in the order synthetic vector, then viral vector.

---

The invention claimed is:

1. A method of vaccination against a viral, bacterial or non-infectious disease comprising administering an effective dose of a prime vaccine and then an effective dose of a boost vaccine, each one of the prime vaccine and the boost vaccine comprising an active principle, wherein:
the prime vaccine comprises, as the active principle, a colloidal synthetic bioresorbable vector comprising at least one protein substance attached to a synthetic vector by inclusion or bonding; and
the boost vaccine comprises, as the active principle, a viral vector comprising at least one nucleotide sequence which codes for a protein substance corresponding to the at least one protein substance of the colloidal synthetic bioresorbable vector.

2. The method according to claim 1, wherein the colloidal synthetic bioresorbable vector is a vector of spherical nature.

3. The method according to claim 1, wherein the colloidal synthetic bioresorbable vector is prepared from at least one polymer selected from the group consisting of poly(a-hydroxy acids), polyhydroxybutyric acids, polycaprolactones, polyorthoesters, and polyanhydrides.

4. The method according to claim 3, wherein the polymer is selected from the group consisting of poly(D-lactic acid), poly(L-lactic acid), polyglycolic acid, a mixture of poly(D- and L-lactic acids), a mixture of poly(L-lactic acid) and polyglycolic acid, a mixture of poly(O-lactic acid) and polyglycolic acid, and a mixture of poly(D- and L-lactic acids) and polyglycolic acid.

5. The method according to claim 1, wherein the colloidal synthetic bioresorbable vector is prepared from at least one natural polymer.

6. The method according to claim 5, wherein the natural polymer is selected from the group consisting of hyaluronic acid, chitosan and dextran.

7. The method according to claim 1, wherein the colloidal synthetic bioresorbable vector comprises protein substances of different types, each constituting an antigen associated with the same disease.

8. The method according to the claim 1, wherein the viral vector is an adenovirus or a poxvirus.

9. The method according to claim 1, wherein the viral vector is a Modified Vaccinia Virus Ankara.

10. The method according to claim 1, wherein the viral vector is the adenovirus 5.

11. The method according to claim 1, wherein the protein substances are of viral origin.

12. The method according to claim 11, wherein the protein substances of viral origin are proteins from a virus selected from the group consisting of herpes viruses, hepatitis viruses, papilloma viruses (HPV), human immunodeficiency viruses (IV), human influenza viruses, and avian influenza viruses.

13. The method according to claim 1, wherein the protein substance is an antigen associated with tumours.

14. The method according to claim 1, wherein the colloidal synthetic bioresorbable vector has a submicron size.

15. The method according to claim 1, wherein the colloidal synthetic bioresorbable vector has a diameter between 150 and 900 nm.

16. The method according to claim 1, wherein the colloidal synthetic bioresorbable vector has a diameter between 250 and 700 nm.

17. The method according to claim 1, wherein the colloidal synthetic bioresorbable vector is free of stabilizer and surfactant.

18. The method according to claim 1, further comprising administering an additional dose of the prime vaccine before the boost vaccine is administered.

* * * * *

SEQUENCE LISTING

```
<160> NUMBER OF SEQ ID NOS: 3

<210> SEQ ID NO 1
<211> LENGTH: 432
<212> TYPE: PRT
<213> ORGANISM: Human immunodeficiency virus

<400> SEQUENCE: 1

Met Ala Ala Arg Ala Ser Ile Leu Ser Gly Gly Glu Leu Asp Arg Trp
1               5                   10                  15

Glu Lys Ile Arg Leu Arg Pro Gly Gly Lys Lys Arg Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ala Ile Gln Thr Gly Ser Glu Glu Leu Lys Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Asp Arg Ile Glu Glu Glu Gln Asn Lys Ser Lys
            100                 105                 110

Gln Lys Ala Gln Pro Ala Ala Ala Asp Lys Gly Asn Ser Ser Gln Ala
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255
```

```
Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Ile Leu Ala Glu Ala Met Ser
            355                 360                 365

Gln Val Thr Asn Ser Ala Thr Ile Met Met Gln Arg Gly Asn Phe Arg
            370                 375                 380

Asn Gln Arg Lys Ile Val Lys Cys Phe Asn Cys Gly Lys Glu Gly His
385                 390                 395                 400

Ile Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
            420                 425                 430

<210> SEQ ID NO 2
<211> LENGTH: 9
<212> TYPE: PRT
<213> ORGANISM: Human immunodeficiency virus

<400> SEQUENCE: 2

Ala Met Gln Met Leu Lys Glu Thr Ile
1               5

<210> SEQ ID NO 3
<211> LENGTH: 9
<212> TYPE: PRT
<213> ORGANISM: Human immunodeficiency virus

<400> SEQUENCE: 3

Thr Pro His Pro Ala Arg Ile Gly Leu
1               5
```